United States Patent
Nathan et al.

(10) Patent No.: US 11,202,829 B2
(45) Date of Patent: *Dec. 21, 2021

(54) METHODS AND COMPOSITIONS FOR ENHANCING THE POTENCY OF SUPERANTIGEN MEDIATED CANCER IMMUNOTHERAPY

(71) Applicant: NeoTX Therapeutics Ltd., Rehovot (IL)

(72) Inventors: Asher Nathan, Jerusalem (IL); Michal Shahar, Rishon Lezion (IL)

(73) Assignee: NeoTX Therapeutics Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,276

(22) Filed: May 14, 2019

(65) Prior Publication Data

US 2020/0078457 A1 Mar. 12, 2020

Related U.S. Application Data

(63) Continuation of application No. 15/402,888, filed on Jan. 10, 2017, now Pat. No. 10,314,910.

(60) Provisional application No. 62/276,955, filed on Jan. 10, 2016.

(51) Int. Cl.
| | |
|---|---|
| *A61K 39/395* | (2006.01) |
| *A61K 39/085* | (2006.01) |
| *C07K 16/28* | (2006.01) |
| *A61K 47/68* | (2017.01) |
| *A61K 39/00* | (2006.01) |
| *A61K 38/16* | (2006.01) |
| *C07K 14/31* | (2006.01) |
| *C07K 16/30* | (2006.01) |

(52) U.S. Cl.
CPC ...... *A61K 39/39558* (2013.01); *A61K 38/164* (2013.01); *A61K 39/0011* (2013.01); *A61K 39/085* (2013.01); *A61K 39/3955* (2013.01); *A61K 39/39541* (2013.01); *A61K 47/6829* (2017.08); *A61K 47/6851* (2017.08); *C07K 14/31* (2013.01); *C07K 16/2818* (2013.01); *C07K 16/30* (2013.01); *C07K 16/3023* (2013.01); *C07K 16/3053* (2013.01); *A61K 2039/505* (2013.01); *A61K 2039/507* (2013.01); *A61K 2039/585* (2013.01); *A61K 2039/6056* (2013.01); *A61K 2039/86* (2018.08); *C07K 2317/24* (2013.01); *C07K 2317/73* (2013.01); *C07K 2317/76* (2013.01); *C07K 2319/40* (2013.01); *C07K 2319/55* (2013.01); *C07K 2319/74* (2013.01)

(58) Field of Classification Search
CPC ............ A61K 47/6829; A61K 47/6855; A61K 39/39558

USPC ............................................ 424/133.1, 134.1
See application file for complete search history.

(56) References Cited

U.S. PATENT DOCUMENTS

| | | |
|---|---|---|
| 5,057,604 A | 10/1991 | Brown |
| 5,220,007 A | 6/1993 | Pederson et al. |
| 5,284,760 A | 2/1994 | Feinstone et al. |
| 5,354,670 A | 10/1994 | Nickoloff et al. |
| 5,366,878 A | 11/1994 | Pederson et al. |
| 5,389,514 A | 2/1995 | Taylor |
| 5,519,114 A | 5/1996 | Johnson et al. |
| 5,545,716 A | 8/1996 | Johnson et al. |
| 5,635,377 A | 6/1997 | Pederson et al. |
| 5,728,388 A | 3/1998 | Terman |
| 5,789,166 A | 8/1998 | Bauer et al. |
| 5,858,363 A | 1/1999 | Dohlsten et al. |
| 5,859,207 A | 1/1999 | Johnson et al. |
| 6,042,837 A | 3/2000 | Kalland et al. |
| 6,126,945 A | 10/2000 | Terman et al. |
| 6,180,097 B1 | 1/2001 | Terman |
| 6,197,299 B1 | 3/2001 | Dohlsten et al. |
| 6,221,351 B1 | 4/2001 | Terman |
| 6,251,385 B1 | 6/2001 | Terman |
| 6,338,845 B1 | 1/2002 | Terman |
| 6,340,461 B1 | 1/2002 | Terman |
| 6,399,332 B1 | 6/2002 | Ulrich et al. |
| 6,447,777 B1 | 9/2002 | Terman et al. |
| 6,514,498 B1 | 2/2003 | Antonsson et al. |
| 6,632,441 B2 | 10/2003 | Schlievert et al. |
| 6,632,640 B1 | 10/2003 | Lee et al. |
| 6,692,746 B1 | 2/2004 | Terman et al. |
| 6,713,284 B2 | 3/2004 | Ulrich et al. |
| 6,774,218 B2 | 8/2004 | Schlievert et al. |
| 6,835,818 B2 | 12/2004 | Schlievert et al. |
| 6,913,755 B2 | 7/2005 | Schlievert et al. |
| 6,926,694 B2 | 8/2005 | Marano-Ford et al. |
| 6,962,694 B1 | 11/2005 | Soegaard et al. |

(Continued)

FOREIGN PATENT DOCUMENTS

| | | |
|---|---|---|
| EP | 1537878 A1 | 6/2005 |
| WO | WO-8907947 A1 | 9/1989 |

(Continued)

OTHER PUBLICATIONS

Shin et al. (Current Opinion in Immunol. 33:25-35 (2015): available online Jan. 23, 2015)).*

(Continued)

*Primary Examiner* — Lynn A Bristol

(74) *Attorney, Agent, or Firm* — Goodwin Procter LLP

(57) ABSTRACT

Provided is a method for enhancing the potency of a targeted cancer immunotherapy in a subject by using a superantigen in combination with a PD-1 inhibitor.

13 Claims, 6 Drawing Sheets

Specification includes a Sequence Listing.

(56) References Cited

U.S. PATENT DOCUMENTS

| | | | |
|---|---|---|---|
| 6,969,616 | B2 | 11/2005 | Hirai et al. |
| 7,087,235 | B2 | 8/2006 | Ulrich |
| 7,094,603 | B2 | 8/2006 | Lawman et al. |
| 7,125,554 | B2 | 10/2006 | Forsberg et al. |
| 7,198,398 | B2 | 4/2007 | Buelow, II et al. |
| 7,226,595 | B2 | 6/2007 | Antonsson et al. |
| 7,226,601 | B1 | 6/2007 | Abrahmsen et al. |
| 7,763,253 | B2 | 7/2010 | Hedlund et al. |
| 8,728,474 | B2 | 5/2014 | Honjo et al. |
| 8,952,136 | B2 | 2/2015 | Carven et al. |
| 9,073,994 | B2 | 7/2015 | Honjo et al. |
| 10,314,910 | B2 * | 6/2019 | Nathan .............. C07K 16/3023 |
| 2001/0046501 | A1 | 11/2001 | Johnson et al. |
| 2002/0051765 | A1 | 5/2002 | Terman |
| 2002/0115190 | A1 | 8/2002 | Chen |
| 2002/0119149 | A1 | 8/2002 | Jakobsen et al. |
| 2002/0141981 | A1 | 10/2002 | Lawman et al. |
| 2002/0142389 | A1 | 10/2002 | Jakobsen et al. |
| 2002/0177551 | A1 | 11/2002 | Terman |
| 2003/0124142 | A1 | 7/2003 | Fraser et al. |
| 2003/0144474 | A1 | 7/2003 | Weidanz et al. |
| 2003/0157113 | A1 | 8/2003 | Terman |
| 2003/0175212 | A1 | 9/2003 | O'Brien et al. |
| 2007/0071675 | A1 | 3/2007 | Wu et al. |
| 2015/0175707 | A1 | 6/2015 | De Jong et al. |
| 2015/0301058 | A1 | 10/2015 | Schettini et al. |
| 2017/0002060 | A1 | 1/2017 | Bolen et al. |
| 2020/0101160 | A1 * | 4/2020 | Nathan .............. C07K 16/3053 |

FOREIGN PATENT DOCUMENTS

| | | |
|---|---|---|
| WO | WO-9301303 A1 | 1/1993 |
| WO | WO-9960119 A2 | 11/1999 |
| WO | WO-9960120 A2 | 11/1999 |
| WO | WO-2003002143 A1 | 1/2003 |
| WO | WO-2003020763 A2 | 3/2003 |
| WO | WO-03/094846 A2 | 11/2003 |
| WO | WO-2006/015882 A2 | 2/2006 |
| WO | WO-2008/156712 A1 | 12/2008 |
| WO | WO-2016/079050 A1 | 5/2016 |

OTHER PUBLICATIONS

"Monoclonal Antibodies Approved by the EMA and FDA for Therapeutic Use (status 2017)" http://www.actip.org/products/monoclonal-antibodies-approved-by-the-ema-and-fda-for-therapeutic-use/.

Ajona et al. (Cancer Discov; 7(7); 694-703 (2017); Published Online First Mar. 13, 2017)).

Amiri et al. (2018) "Anticancer Effects of Doxorubicin-Loaded Micelle on MCF-7 and MDAMB-231, Breast Cancer Cell Lines," Journal of Research in Medical and Dental Science, 6(2): 298-304.

Beckman et al. (Can. 109:170-179 (2007)).

Borghaei et al. (2009) "Phase I dose escalation, pharmacokinetic and pharmacodynamic study of naptumomab estafenatox alone in patients with advanced cancer and with docetaxel in patients with advanced non-small-cell lung cancer," J. Clin. Oncol., 27(25):4116-23.

Buchbinder et al. (2016) "CTLA-4 and PD-1 Pathways: Similarities, Differences, and Implications of Their Inhibition," Am. J. Clin. Oncol. 39(1):98-106.

Cell Line Profile (Jun. 2017) "MDA-MB-231 (ECACC catalogue No. 92020424)," European Collection of Authenticated Cell Cultures (ECACC), 3 pages.

Cespdes et al. (Clin. Transl. Oncol. 8(5):318-329 (2006)).

Chen et al. (2012) "Targeting the epidermal growth factor receptor in non-small cell lung cancer cells: the effect of combining RNA interference with tyrosine kinase inhibitors or cetuximab," BMC Med. 10:28 (15 pages).

Cohen et al. (2007) "An open label phase I study of ABR-217620 in combination with docetaxel in patients with NSCLC," AACR-NCI-EORTC International Conference: Molecular Targets and Cancer Therapeutics.

Cubas et al. (2018) "Chemotherapy Combines Effectively with Anti-PD-L1 Treatment and Can Augment Antitumor Responses," J. Immunol., 201(8): 2273-2286.

Curran et al. (2009) "PD-1 and CTLA-4 combination blockade expands infiltrating T cells and reduces regulatory T and myeloid cells within B16 melanoma tumors," PNAS, 107(9): 4275-4280.

Database WPI Week 199742, Thomson Scientific, London, GB (1 page).

Dennis (Nature 442:739-741 (2006)).

Dohlsten et al. (1991) "Monoclonal antibody-targeted superantigens: a different class of anti-tumor agents," Proc. Natl. Acad. Sci. USA, 88:9287-9291.

Dohlsten et al. (1994) "Monoclonal antibody-superantigen fusion proteins: tumor-specific agents for T-cell-based tumor therapy," Proc. Natl. Acad. Sci. USA, 91:8945-8949.

Dohlsten et al. (1995) "Antibody-targeted superantigens are potent inducers of tumor-infiltrating T lymphocytes in vivo," Proc. Natl. Acad. Sci. USA, 92:9791-9795.

Eisen et al. (2013) "Baseline biomarker trend analysis of a randomized phase 2/3 study of naptumomab estafenatox plus IFN-α vs IFN-α in advanced renal cell carcinoma" European Cancer Congress.

Eisen et al. (2014) "Naptumomab estafenatox: targeted immunotherapy with a novel immunotoxin," Curr. Oncol. Rep., 16(2):370.

Elkord et al. (2015) "Immunological response and overall survival in a subset of advanced renal cell carcinoma patients from a randomized phase 2/3 study of naptumomab estafenatox plus IFN-α versus IFN-α" Oncotarget, 6(6):4428-39.

Erlandsson et al. (2003) "Identification of the antigenic epitopes in staphylococcal enterotoxins A and E and design of a superantigen for human cancer therapy," J. Mol. Biol., 333:893-905.

Evans et al. (2015) "Antibody Blockade of Semaphorin 4D Promotes Immune Infiltration into Tumor and Enhances Response to Other Immunomodulatory Therapies," Cancer Immunology Research, 3(6): 689-701.

Fagnoni et al. (2002) "T-cell dynamics after high-dose chemotherapy in adults: elucidation of the elusive $CD8^+$ subset reveals multiple homeostatic T-cell compartments with distinct implications for immune competence," Immunology, 106: 27-37.

Forsberg et al. (1997) "Identification of framework residues in a secreted recombinant antibody fragment that control production level and localization in Escherichia coli," J. Biol. Chem., 272:12430-12436.

Fujimori et al. (J. Nuc. Med. 31 :1191-1198 (1990)).

Giavazzi et al. (2014) "Syngeneic Murine Metastasis Models: B16 Melanoma," Methods Mol. Biol. 1070: 131-40.

Hawkins et al. (2013) "A randomized phase 2/3 study of naptumomab estafenatox plus IFN-α vs IFN-α in advanced renal cell carcinoma" American Society for Clinical Oncology Annual Meeting.

Hedlund et al. (2013) "Tumor-Targeted Superantigens," Fusion Protein Technologies for BiopharmaceuticalsL Applications and Challenges, First Edition, 365-381.

Hu et al. (2018) "Improving immunotherapy for colorectal cancer using dendritic cells combined with anti-programmed death-ligand in vitro," Oncol. Lett. 15(4): 5345-5351.

Huang et al. (Appl Microbiol Biotechnol (2010) 87:401-410).

International Search Report for International Patent Application No. PCT/IB2017/000511, dated Aug. 8, 2017 (6 pages).

Jiao et al. (2017) "PARP Inhibitor Upregulates PD-L1 Expression and Enhances Cancer-Associated Immunosuppression," Clin. Cancer Res. 23(14): 3711-3720.

Juneja et al. (2017) "PD-L1 on tumor cells is sufficient for immune evasion in immunogenic tumors and inhibits CD8 T cell cytotoxicity," J. Exp. Med. 214(4):895-904.

Keir et al. (2008) "PD-1 and its ligands in tolerance and immunity," Annu. Rev. Immunol., 26:677-704.

Kraft et al. (1985) "Staphylococcal Protein A Bound to Sepharose 4B Is Mitogenic for T Cells but Not B Cells from Rabbit Tissues," Clinical Immunology and Immunopathology, 37: 13-21.

Li et al. (2008) "BIBW2992, an irreversible EGFR/HER2 inhibitor highly effective in preclinical lung cancer models," Oncogene, 27(34): 4702-4771.

(56) References Cited

OTHER PUBLICATIONS

Lin et al. (2019) "Flubendazole demonstrates valid antitumor effects by inhibiting STAT3 and activating autophagy," Journal of Experimental & Clinical Cancer Research, 38(1): 293, 13 pages.

Mahoney et al. (2015) "Combination cancer immunotherapy and new immunomodulatory targets," Nat. Rev. Drug Discov., 14:561-584.

Marrack et al. (1990) "The *staphylococcal* enterotoxins and their relatives," Science, 248(4956)705-11.

Mondal et al. (2001) "Synergistic Immunopotentiating Effects Indcued by T-Cell and B-Cell Superantigen in Mice," Immunological Investigations, 30(3): 169-180.

Ngiow et al. (2015) "A Threshold Level of Intratumor CD8+ T-cell PD1 Expression Dictates Therapeutic Response to Anti-PD1," Cancer Research, 75(18): 3800-3811.

Ngiow et al. (2016) "Agonistic CD40 mAb-Driven IL12 Reverses Resistance to Anti-PD1 in a T-cell-Rich Tumor," Cancer Research, 76(21): 6266-6277.

Overwijk et al. (2001) "B16 as a mouse model for human melanoma," Curr. Protoc. Immunol. 20:20.1.

Rizvi et al. (2015) "Cancer immunology. Mutational landscape determines sensitivity to PD-1 blockade in non-small cell lung cancer," Science, 348(6230):124-8.

Rosenberg (2014) "IL-2: the first effective immunotherapy for human cancer," J. Immunol. 192(12):5451-8.

Rosenberg et al. (1985) "Regression of established pulmonary metastases and subcutaneous tumor mediated by the systemic administration of high-dose recombinant interleukin 2," J. Exp. Med. 161 (5):1169-88.

Rudnick et al. (Can. Biotherp. & Radiopharm. 24: 155-162 (2009)).

Selby et al. (2013) "Anti-CTLA-4 antibodies of IgG2a isotype enhance antitumor activity through reduction of intratumoral regulatory T cells," Cancer Immunol. Res., 1(1):32-42.

Si et al. (2006) "Gene therapy by membrane-expressed superantigen for α-fetoprotein-producing hepatocellular carcinoma," Gene Therapy, 13: 1603-1610.

Stern et al. (2016) "5T4 oncofoetal antigen: an attractive target for immune intervention in cancer," Cancer Immunol. Immunother. (12 pages).

Sundstedt et al. (2012) "Monotherapeutically nonactive CTLA-4 blockade results in greatly ehhanced antitumor effects when combined with tumor-targeted superantigens in a B16 melanoma model," J. Immunother., 35:344-35.

Talmadge et al. (Am. J. Pathol 170(3):793-804 (2007)).

Tang et al. (2018) "Tumor cell versus host immune cells: whose PD-L1 contributes to PD-1/PD-L1 blockade medaited cancer immunotherapy?" Cell Biosci., 8(34): 8 pages.

Thurber et al. (Adv. Drug Deliv. Rev. 60:1421-1434 (2008)).

Touil et al. (2014) "Colon Cancer Cells Escape 5FU Chemotherapy-Induced Cell Death by Entering Stemness and Quiescence Associated with the c-Yes/YAP Axis," Clin. Cancer Res., 20(4):837-46.

Voskoglou-Nomikos (Clin. Can. Res. 9:4227-4239 (2003)).

Written Opinion for International Patent Application No. PCT/IB2017/000511, dated Aug. 8, 2017 (8 pages).

www.medsafe.govt.nz/Profs/Datasheet/o/opdivoinf.pdf (product data sheet for nivolumab; pp. 1-47; printed Jul. 5, 2017).

Yeo et al. (2010) "Erlotinib as a Dose of 25 mg Daily for Non-small Cell Lung Cancers with EGFR Mutations," J. Thorac. Oncol. 5(7): 1048-1052.

\* cited by examiner

```
                                              A            B
SEQ ID NO:  3 SEA/E-120  SEKSEEINEKDLRKKSELQGTALGNLKQIYYYNSKAITSSEKSADQFLTNTLLFKGFFTG  60
SEQ ID NO: 10 SEA/E-18   SEKSEEINEKDLRKKSELQGTALGNLKQIYYYNEKAITENKESDDQFLENTLLFKGFFTG  60
SEQ ID NO:  1 SEE        SEKSEEINEKDLRKKSELQRNALSNLRQIYYYNEKAITENKESDDQFLENTLLFKGFFTG  60
SEQ ID NO:  2 SEA        SEKSEEINEKDLRKKSELQGTALGNLKQIYYYNEKAKTENKESHDQFLQHTILFKGFFTD  60
                         ******************* .**.**:******.** *..::* **** :*:*******.

C
              SEA/E-120  HPWYNDLLVDLGSTAATSEYEGSSVDLYGAYYGYQCAGGTPNKTACMYGGVTLHDNNRLT 120
              SEA/E-18   HPWYNDLLVDLGSKDATNKYKGKKVDLYGAYYGYQCAGGTPNKTACMYGGVTLHDNNRLT 120
              SEE        HPWYNDLLVDLGSKDATNKYKGKKVDLYGAYYGYQCAGGTPNKTACMYGGVTLHDNNRLT 120
              SEA        HSWYNDLLVDFDSKDIVDKYKGKKVDLYGAYYGYQCAGGTPNKTACMYGGVTLHDNNRLT 120
                         *.********:.*.   ..:*:*..************************************

SEA/E-120  EEKKVPINLWIDGKQTTVPIDKVKTSKKEVTVQELDLQARHYLHGKFGLYNSDSFGGKVQ 180
              SEA/E-18   EEKKVPINLWIDGKQTTVPIDKVKTSKKEVTVQELDLQARHYLHGKFGLYNSDSFGGKVQ 180
              SEE        EEKKVPINLWIDGKQTTVPIDKVKTSKKEVTVQELDLQARHYLHGKFGLYNSDSFGGKVQ 180
              SEA        EEKKVPINLWLDGKQNTVPLETVKTNKKNVTVQELDLQARRYLQEKYNLYNSDVFDGKVQ 180
                         **********:****.***::.***.**:***********:**: *:.***** *.****

D                            E
              SEA/E-120  RGLIVFHSSEGSTVSYDLFDAQGQYPDTLLRIYRDNTTISSTSLSISLYLYTT 233
              SEA/E-18   RGLIVFHSSEGSTVSYDLFDAQGQYPDTLLRIYRDNKTINSENLHIALYLYTT 233
              SEE        RGLIVFHSSEGSTVSYDLFDAQGQYPDTLLRIYRDNKTINSENLHIDLYLYTT 233
              SEA        RGLIVFHTSTEPSVNYDLFGAQGQYSNTLLRIYRDNKTINSENMHIDIYLYTS 233
                         *******:*  .:*.****.*****.:*********.**.* .: * :****:
```

FIGURE 2

5T4 Variable Heavy chain

SEQ ID NO: 7  1-50    EVQLQ QSGPD LVKPG ASVKI SCKAS GYSFT GYYMH WVKQS PGKGL EWIGR
51-100   INPNN GVTLY NQKFK DKATL TVDKS STTAY MELRS LTSED SAVYY CARST
101-150  MITNY VMDYW GQGTS VTVSS AKTTP PSVYP LAPGS AAQTN SMVTL GCLVK
         *C242 Constant Heavy chain*
151-200  GYFPE PVTVT WNSGS LSSGV HTFPA VLQSD LYTLS SSVTV PSSTW PSETV
                                                     *SEA/E-120*
201-250  TCNVA HPASS TKVDK KIVPR DSGGP SEKSE EINEK DLRKK SELQG TALGN
251-300  LKQIY YNSK ATTSS EKSAD QFLTN TLLFK GFFTG HEWYN DLLVD LGSTA
301-350  ATSEY EGSSV DLYGA VVGYQ CAGGT PNKTA CMYGG VILHD NNRLT EEKKV
351-400  PINLW IDGKQ TTVPT DKVKT SKKEV TVQEL DLQAR HYLHG KFGLY NSDSF
401-450  GGKVQ RGLIV FHSSE GSTVS YDLED AQGQY PDTLL RIYRD NTTIS STSLS
451-459  ISLYL YTT

5T4 Variable Light chain

459-500                           SI VMTQT PTSLL VSAGD RVTIT CKASQ SVSND VAWYQ QKPGQ
501-550  SPKLL ISYTS SRYAG VPDRF SGSGY GTDFT LTISS VQAED AAVYF CQQDY
                                       *C242 Constant Light chain*
551-600  NSPPT FGGGT KLEIK RADAA PTVSI FPPSS EQLTS GGASV VCFLN NFYPK
601-650  DINVK WKIDG SERQN GVLNS WTDQD SKDST YSMSS TLTLT KDEYE RHNSY
651-672  TCEAT HKTST SPIVK SFNRN ES

FIGURE 3

METHODS AND COMPOSITIONS FOR ENHANCING THE POTENCY OF SUPERANTIGEN MEDIATED CANCER IMMUNOTHERAPY

CROSS REFERENCE TO RELATED APPLICATIONS

This application is a continuation of U.S. patent application Ser. No. 15/402,888, filed Jan. 10, 2017, which claims the benefit of, and priority to, U.S. Provisional Patent Application Ser. No. 62/276,955, filed Jan. 10, 2016, the entire contents of which are hereby incorporated by reference in their entirety.

FIELD OF THE INVENTION

The invention relates generally to methods and compositions for enhancing the potency of superantigen mediated cancer immunotherapy, and more specifically relates to superantigen mediated cancer immunotherapy with an immunopotentiator that prevents cancer cells from evading the subject's immune system.

BACKGROUND

According to the American Cancer Society, more than one million people in the United States are diagnosed with cancer each year. Cancer is a disease that results from uncontrolled proliferation of cells that were once subject to natural control mechanisms but have been transformed into cancerous cells that continue to proliferate in an uncontrolled manner. In recent years, a number of immunotherapies have been developed that have attempted to harness the subject's immune system to find and destroy cancer cells. Such immunotherapies include, for example, those that are designed to boost the body's natural defenses for fighting cancer using natural molecules made by the body, or alternatively, through administration of recombinant molecules designed to improve, better target or restore immune system function. Certain immunotherapies include the administration of compounds known to be general immune system enhancers, such as cytokines, for example, IL-2 and interferon. While various immunotherapies developed to date have shown efficacy, they can be associated with side effects including, for example, off-target activities, allergic reactions to the active agents administered including the potential for cytokine storms, a loss of potency caused by the stimulation of antibodies that bind and neutralize the active agents, a decrease in blood cell number, and fatigue.

Other immunotherapies utilize molecules referred to as immune checkpoint inhibitors, which enhance immune responses to cancer. Such checkpoint inhibitors function to inhibit the ability of cancer cells to block immune inhibitory checkpoints thereby resulting in an enhancement of potency of an anti-cancer therapy. A first-generation immune checkpoint inhibitor ipilimumab (YERVOY®; Bristol-Myers Squibb) was approved by the U.S. Food and Drug Administration in 2011 and is an IgG1 monoclonal antibody that can cause ADCC-mediated regulatory T-cell (Treg) cytotoxicity. Over the years, immunochemotherapy, the combination of immunotherapy and chemotherapy, has become important in the treatment of certain cancers. For example, rituximab (RITUXAN®; Roche) is a CD-20-specific monoclonal antibody that depletes CD20-expressing cells and has become a standard component of the treatment of B-cell lymphomas, for example, non-Hodgkin's lymphoma using rituximab (R), cyclophosphamide (C), hydroxydaunorubicin (H), oncovin (O), and prednisone (P), known as R-CHOP.

Recently, PD-1 inhibitors have been approved such as Nivolumab and Pembrolizumab, which prevent the inhibitory signals between PD-1 and PD-L1. While these drugs have potentiated durable responses in some patients, the response rates of these drugs as monotherapy have been low and in the range of 21%, and the complete response rate has been about 1% in several studies.

Although there are ongoing efforts to combine various cancer therapies to improve patient outcomes and some combinations have shown benefits in efficacy, safety has become a major concern as combining drugs may potentiate serious side effects. For example, drug-related adverse events of grade 3 or 4 were reported in a significant number of patients who received anti-CTLA-4 and anti-PD1 antibodies in combination as compared to patients who received the anti-CTLA-4 antibody alone. Accordingly, despite the significant developments that have been made in the fields of immunotherapy and oncology, there is still a need for safe and effective immunotherapies for treating cancer.

SUMMARY OF THE INVENTION

In recent years, a number of immunotherapies have been developed that have attempted to harness the subject's immune system to find and destroy cancer cells. Although a human immune system has the potential to eliminate cancer cells, certain cancer cells develop the ability to "turn off," "down regulate," or otherwise evade the host's immune system allowing the cancerous cells to continue to grow and proliferate unchecked.

The invention is based, in part, upon the discovery that a targeted immune response against a cancer in a subject can be significantly enhanced by combining a superantigen-based therapy with an immunopotentiator that can (a) stimulate activating T-cell signaling, (b) repress T-cell inhibitory signalling between the cancerous cells and a T-cell, (c) repress inhibitory signalling that leads to T-cell expansion, activation and/or activity via a human IgG4 immunoglobulin-mediated pathway, or (d) a combination of two or more of the foregoing.

In one aspect, the invention provides a method of treating a cancer in a subject in need thereof. The method comprises administering to the subject (i) an effective amount of a superantigen conjugate, the conjugate comprising a superantigen covalently linked to a targeting moiety that binds a first antigen preferentially expressed by cancerous cells within the subject, and (ii) an effective amount of an immunopotentiator (for example, a checkpoint pathway inhibitor) effective to at least one or more of (a) stimulating activating T-cell signaling, (b) repressing T-cell inhibitory signalling between the cancerous cells and a T-cell, and/or (c) repressing inhibitory signalling that leads to T-cell expansion, activation and/or activity via human IgG4 immunoglobulin-mediated pathway (i.e., via a non-human IgG1-mediated immune response pathway), thereby to potentiate an immune response in the subject against the cancerous cells to treat the cancer. Superantigen-based therapies may upregulate the secretion of interferon γ from T-cells, which in turn may upregulate PD-L1 expression. However, to date, it was not known if this negative effect could be mitigated by a PD-1 inhibitor that offsets the positive effects of increased antigenicity. It has now been discovered that superantigen conjugate-based therapies can potentially effect response rates of PD1 inhibitors or otherwise effect clinical outcome.

In certain embodiments, the superantigen conjugate may be administered to the subject before, at the same time as, or after the immunopotentiator. Furthermore, the superantigen conjugate and the immunopotentiator may be co-administered together or sequentially with one or more additional agents that enhance the potency and/or selectively of the therapeutic effect. Such agents include, for example, corticosteroids, additional immune modulators, and those compounds designed to reduce the patient's possible immunoreactivity to the administered superantigen conjugate. For example, immunoreactivity to the administered superantigen may be reduced via co-administration with, for example, an anti-CD20 antibody and/or an anti-CD19 antibody, that reduces the production of anti-superantigen antibodies in the subject.

In certain embodiments, the superantigen present in the superantigen conjugate binds to a T-cell receptor on a surface of a T-cell, for example, a $CD4^+$ and/or a $CD8^+$ T-cell. The superantigen can comprise Staphylococcal enterotoxin A or B, an immunologically reactive variant thereof, or an immunologically reactive fragment of the Staphylococcal enterotoxin A or B or the immunologically variant thereof. The targeting moiety of the conjugate binds an antigen preferably expressed on the cancer cell thereby to bind the superantigen to the cancer cell. The targeting moiety can be used to target the conjugate to the cancerous cells by preferentially binding one or more different antigens, for example, one or more cell surface antigens, expressed by the cancerous cells. In certain embodiments, the cell surface antigen is, for example, a 5T4 oncofetal cancer antigen, which is present on cancer cells as well as certain cancer stem cells. Although a variety of targeting moieties can be used to target the superantigen to the cancerous cells expressing the first antigen, in certain embodiments, the targeting moiety is an antibody, for example, an anti-5T4 antibody. In certain embodiments, the targeting moiety is a Fab fragment that binds 5T4. In certain embodiments, the superantigen in the conjugate comprises amino acids 226-458 of SEQ ID NO: 7 (also residues 226-458 of SEQ ID NO: 8), or an immunologically reactive variant thereof, or an immunologically reactive fragment of each of the foregoing.

In certain embodiments, the immunopotentiator is a checkpoint pathway inhibitor. For example, in certain embodiments, the immunopotentiator reduces expression of, or activity of, a Programmed Cell Death-Ligand (PD-L), for example, PD-L1 or PD-L2, expressed on the surface of the cancerous cells. PD-L is a ligand that binds to a Programmed Cell Death-1 receptor (PD-1), which is expressed on T-cells. Certain cancer cells express PD-L to reduce the activation or activity of T-cells via a PD-1 checkpoint pathway so as to evade the subject's immune system. In certain embodiments, the immunopotentiator is an anti-PD-1 antibody that prevents PD-L, for example, PD-L1 or PD-L2, from binding to PD-1 expressed on the surface of the T-cell. In certain embodiments, the anti-PD-1 antibody has or is based on a human IgG4 immunoglobulin isotype that induces much lower antibody-dependent cell-mediated toxicity (ADCC) than a human IgG1 immunoglobulin isotype.

In certain embodiments, the anti-PD-1 antibody is selected from the group consisting of nivolumab and pembrolizumab. Other PD-1 inhibitors include (i) anti-PD-1 antibodies, for example, MK-3475 (Merck & Co), pidlizumab (CureTech), AMP-224 (AstraZeneca/Medimmune) and AMP-514 (AstraZeneca/Medimmune), and (ii) anti-PD-L1 antibodies, for example, MPDL3280A (Genentech/Roche), MEDI-4736 (AstraZeneca/Medimmune) and MSB0010718C (EMD Serono/Merck KGA).

In certain embodiments, other potential immunopotentiators can be used such as a 4-1BB (CD137) agonist (e.g., the fully human IgG4 anti-CD137 antibody Urelumab/BMS-663513), a LAG3 inhibitor (e.g., the humanized IgG4 anti-LAG3 antibody LAG525, Novartis); an IDO inhibitor (e.g., the small molecule INCB024360, Incyte Corporation), a TGFβ inhibitor (e.g., the small molecule Galunisertib, Eli Lilly) and other receptor or ligands that are found on T-cells and/or tumor cells and that are amenable to pharmaceutical intervention based on agonist/antagonist interactions but not through ADCC.

It is understood that the method can be used to treat a variety of cancers, for example, a cancer selected from the group consisting of breast cancer, cervical cancer, colorectal cancer, gastric cancer, non-small cell lung cancer, ovarian cancer, pancreatic cancer, prostate cancer, renal cell cancer, and skin cancer.

In another aspect, the invention provides a pharmaceutical composition comprising (i) an effective amount of a superantigen conjugate, the conjugate comprising a superantigen covalently linked to a targeting moiety that binds to a first antigen expressed by cancerous cells in a subject, (ii) an effective amount of an immunopotentiator effective to at least one or more of the following (a) stimulating activating T-cell signaling, (b) repressing T-cell inhibitory signalling between the cancerous cells and a T-cell, and/or (c) repressing inhibitory signalling that leads to T-cell expansion, activation and/or activity via a human IgG4 immunoglobulin-mediated pathway (i.e., via a non-human IgG1-mediated immune response pathway), in the subject, and (iii) a pharmaceutically acceptable excipient.

In certain embodiments, the superantigen component of the conjugate binds to a T-cell receptor expressed on a cell surface of a T-cell. For example, in certain embodiments, the superantigen comprises Staphylococcal enterotoxin A or Staphylococcal enterotoxin B, an immunologically reactive variant thereof, or an immunologically reactive fragment of the Staphylococcal enterotoxin A or B or the variant thereof. It is understood that the targeting moiety in the conjugate can target the conjugate to one or more antigens expressed in the cancerous cells. In certain embodiments, the first antigen targeted by the conjugate is a cell surface antigen, for example, a 5T4 oncofetal cancer antigen. Although a variety of targeting moieties can be used to target the conjugate to the antigen expressed in the cancerous cells, in one embodiment, the targeting moiety is an antibody, for example, an anti-5T4 antibody. In certain embodiments, the targeting moiety comprises a Fab fragment that binds the 5T4 antigen. In certain embodiments, the superantigen in the conjugate comprises amino acid residues 226-458 of sequence of SEQ ID NO: 7 (also residues 226-458 of SEQ ID NO: 8) or an immunologically reactive variant thereof, or an immunologically reactive fragment of each of the foregoing.

In certain embodiments, the immunopotentiator prevents PD-L (for example, PD-L1 or PD-L2) expressed in the cancerous cells from binding a PD-1 receptor expressed on the T-cell so as to reduce the activation and/or activity of the T-cell. For example, the immunopotentiator can be a PD-1 checkpoint pathway inhibitor, for example, an anti-PD-1 antibody. In certain embodiments, the anti-PD-1 antibody has or is based on a human immunoglobulin IgG4 isotype that preferably induces much lower ADCC than a human IgG1 immunoglobulin isotype. In certain embodiments, the anti-PD-1 antibody is selected from the group consisting of nivolumab and pembrolizumab.

These and other aspects and features of the invention are described in the following detailed description, figures, and claims.

BRIEF DESCRIPTION OF THE DRAWINGS

The foregoing and other objects, features and advantages of the invention will become apparent from the following description of preferred embodiments, as illustrated in the accompanying drawings. Like referenced elements identify common features in the corresponding drawings. The drawings are not necessarily to scale, with emphasis instead being placed on illustrating the principles of the present invention, in which:

FIG. 2 is a sequence alignment showing the homologous A-E regions in certain wild type and modified superantigens;

FIG. 3 is an amino acid sequence corresponding to an exemplary superantigen conjugate, naptumomab estafenatox/ANYARA®, which comprises two protein chains. The first protein chain comprises residues 1 to 458 of SEQ ID NO: 7 (see also, SEQ ID NO: 8), and includes a chimeric 5T4 Fab heavy chain, corresponding to residues 1 to 222 of SEQ ID NO: 7, and the SEA/E-120 superantigen, corresponding to residues 226 to 458 of SEQ ID NO: 7, covalently linked via a GGP tripeptide linker, corresponding to residues 223-225 of SEQ ID NO: 7. The second chain comprises residues 459 to 672 of SEQ ID NO: 7 (see also, SEQ ID NO: 9) and includes a chimeric 5T4 Fab light chain. The two protein chains are held together by non-covalent interactions between the Fab heavy and light chains;

DETAILED DESCRIPTION

Figure 1:
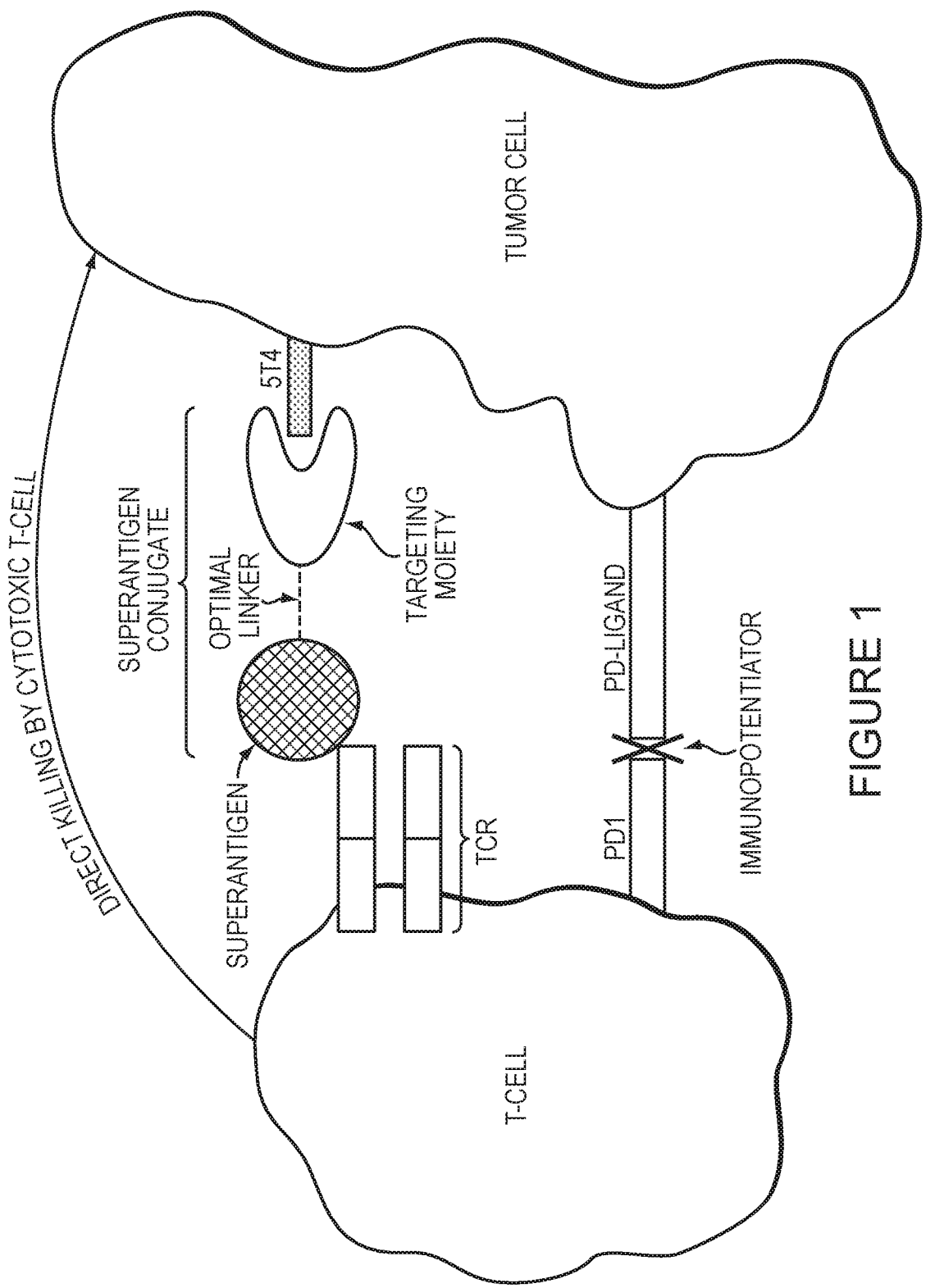
FIG. 1 is a schematic representation of an exemplary treatment method of the invention using a superantigen conjugate and an immunopotentiator.

The present invention relates to methods and compositions for treating cancer in a subject. In particular, the invention is based, in part, upon the discovery that a targeted immune response against a cancer in a subject can be significantly enhanced by combining a superantigen-based therapy with an immunopotentiator that can (a) stimulate activating T-cell signaling, (b) repress T-cell inhibitory signalling between the cancerous cells and a T-cell, (c) repress inhibitory signalling that leads to T-cell expansion, activation and/or activity via a human IgG4 immunoglobulin-mediated pathway, or (d) a combination of two or more of the foregoing. It has been discovered that the administration of a tumor-targeted superantigen (TTS; a form of immunotherapy), together with an immunopotentiator (e.g., a PD-1 inhibitor), can result in enhanced anti-cancer effect for both the superantigen and the immunopotentiator when combined together (i.e., the agents act synergistically) to produce an effect that is greater than the additive effect of each agent when administered alone.

In one aspect, the invention provides a method of treating a cancer in a subject in need thereof. The method comprises administering to the subject (i) an effective amount of a superantigen conjugate, the conjugate comprising a superantigen covalently linked to a targeting moiety that binds a first antigen preferentially expressed by cancerous cells within the subject, and (ii) an effective amount of an immunopotentiator (for example, a checkpoint pathway inhibitor) effective to at least one or more of (a) stimulating activating T-cell signaling, (b) repressing T-cell inhibitory signalling between the cancerous cells and a T-cell, and/or (c) repressing inhibitory signalling that leads to T-cell expansion, activation and/or activity via a human IgG4 immunoglobulin-mediated pathway (i.e., via a non-human IgG1-mediated immune response pathway), thereby to potentiate an immune response in the subject against the cancerous cells to treat the cancer.

In another aspect, the invention provides a pharmaceutical composition comprising (i) an effective amount of a superantigen conjugate, the conjugate comprising a superantigen covalently linked to a targeting moiety that binds to a first antigen expressed by cancerous cells in a subject, (ii) an effective amount of an immunopotentiator effective to at least one or more of (a) stimulating activating T-cell signaling, (b) repressing T-cell inhibitory signalling between the cancerous cells and a T-cell, and/or (c) repressing inhibitory signalling that leads to T-cell expansion, activation and/or activity via a human IgG4 immunoglobulin-mediated pathway (i.e., via a non-human IgG1-mediated immune response pathway), in the subject, and (iii) a pharmaceutically acceptable excipient.

I. Definitions

Unless defined otherwise, technical and scientific terms used herein have the same meaning as commonly understood by one of ordinary skill in the art to which this invention belongs. For purposes of the present invention, the following terms are defined below.

As used herein, the terms "a" or "an" may mean one or more. For example, a statement such as "treatment with a superantigen and an immunopotentiator," can mean treatment: with one superantigen and one immunopotentiator; with more than one superantigen and one immunopotentiator; with one superantigen and more than one immunopotentiator; or with more than one superantigen and more than one immunopotentiator.

As used herein, unless otherwise indicated, the term "antibody" is understood to mean an intact antibody (e.g., an intact monoclonal antibody) or antigen-binding fragment of an antibody, including an intact antibody or antigen-binding fragment of an antibody (e.g., a phage display antibody including a fully human antibody, a semisynthetic antibody or a fully synthetic antibody) that has been optimized, engineered or chemically conjugated. Examples of antibodies that have been optimized are affinity-matured antibodies. Examples of antibodies that have been engineered are Fc optimized antibodies, antibodies engineered to reduce immunogenicity, and multi-specific antibodies (e.g., bispecific antibodies). Examples of antigen-binding fragments include Fab, Fab', F(ab')$_2$, Fv, single chain antibodies (e.g., scFv), minibodies and diabodies. An antibody conjugated to a toxin moiety is an example of a chemically conjugated antibody.

As used herein, the terms "cancer" and "cancerous" are understood to mean the physiological condition in mammals that is typically characterized by unregulated cell growth. Examples of cancer include, but are not limited to, melanoma, carcinoma, lymphoma, blastoma, sarcoma, and leukemia or lymphoid malignancies. More particular examples of cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, bone cancer, brain cancer, retinoblastoma, endometrial cancer or uterine carcinoma, salivary gland carcinoma, kidney or renal cancer, prostate cancer, vulval cancer, thyroid cancer, hepatic carcinoma, anal carcinoma, penile carcinoma, testicular cancer, as well as head and neck cancer, gum or tongue cancer. The cancer comprises cancer or cancerous cells, for example, the cancer may comprise a plurality of individual cancer or cancerous cells, for example, a leukemia, or a tumor comprising a plurality of associated cancer or cancerous cells.

As used herein, the term "immunogen" is a molecule that provokes (evokes, induces, or causes) an immune response. This immune response may involve antibody production, the activation of certain cells, such as, for example, specific immunologically-competent cells, or both. An immunogen may be derived from many types of substances, such as, but not limited to, molecules from organisms, such as, for example, proteins, subunits of proteins, killed or inactivated whole cells or lysates, synthetic molecules, and a wide variety of other agents both biological and nonbiological. It is understood that essentially any macromolecule (including naturally occurring macromolecules or macromolecules produced via recombinant DNA approaches), including virtually all proteins, can serve as immunogens.

As used herein, the term "immunogenicity" relates to the ability of an immunogen to provoke (evoke, induce, or cause) an immune response. Different molecules may have differing degrees of immunogenicity, and a molecule having an immunogenicity that is greater compared to another molecule is known, for example, to be capable of provoking (evoking, inducing, or causing) a greater immune response than would an agent having a lower immunogenicity.

As used herein, the term "antigen" as used herein refers to a molecule that is recognized by antibodies, specific immunologically-competent cells, or both. An antigen may be derived from many types of substances, such as, but not limited to, molecules from organisms, such as, for example, proteins, subunits of proteins, nucleic acids, lipids, killed or inactivated whole cells or lysates, synthetic molecules, and a wide variety of other agents both biological and nonbiological.

As used herein, the term "antigenicity" relates to the ability of an antigen to be recognized by antibodies, specific immunologically-competent cells, or both.

As used herein, the term "major histocompatibility complex," or "MHC," refers to a specific cluster of genes, many of which encode evolutionarily related cell surface proteins involved in antigen presentation, that are important determinants of histocompatibility. Class I MHC, or MHC-I, function mainly in antigen presentation to CD8$^+$ T lymphocytes (CD8$^+$ T-Cells). Class II MHC, or MHC-II, function mainly in antigen presentation to CD4$^+$ T lymphocytes (CD4$^+$ T-Cells).

As used herein, the term "derived," for example "derived from," includes, but is not limited to, for example, wild-type molecules derived from biological hosts such as bacteria, viruses and eukaryotic cells and organisms, and modified molecules, for example, modified by chemical means or produced in recombinant expression systems.

As used herein, the terms "seroreactive," "seroreaction" or "seroreactivity" are understood to mean the ability of an agent, such as a molecule, to react with antibodies in the serum of a mammal, such as, but not limited to, a human. This includes reactions with all types of antibodies, including, for example, antibodies specific for the molecule and nonspecific antibodies that bind to the molecule, regardless of whether the antibodies inactivate or neutralize the agent. As is known in the art, different agents may have different seroreactivity relative to one another, wherein an agent having a seroreactivity lower than another would, for example, react with fewer antibodies and/or have a lower affinity and/or avidity to antibodies than would an agent having a higher seroreactivity. This may also include the ability of the agent to elicit an antibody immune response in an animal, such as a mammal, such as a human.

As used herein, the terms "soluble T-cell receptor," or "soluble TCR," are understood to mean a "soluble" T-cell receptor comprising the chains of a full-length (e.g., membrane bound) receptor, except that the transmembrane region of the receptor chains are deleted or mutated so that the receptor, when expressed by a cell, will not insert into, traverse or otherwise associate with the membrane. A soluble T-cell receptor may comprise only the extracellular domains or extracellular fragments of the domains of the wild-type receptor (e.g., lacks the transmembrane and cytoplasmic domains).

As used herein, the term "superantigen" is understood to mean a class of molecules that stimulate a subset of T-cells by binding to MHC class II molecules and Vβ domains of T-cell receptors, thereby activating T-cells expressing particular Vβ gene segments. The term includes wild-type, naturally occurring superantigens, for example, those isolated from certain bacteria or expressed from unmodified genes from same, as well as modified superantigens, wherein, for example, the DNA sequence encoding a superantigen has been modified, for example, by genetic engineering, to, for example, produce a fusion protein with a targeting moiety, and/or alter certain properties of the superantigen, such as, but not limited to, its MHC class II binding (for example, to reduce affinity) and/or its seroreactivity, and/or its immunogenicity, and/or antigenicity (for example, to reduce its seroreactivity). The definition includes wild-type and modified superantigens and any immunologically reactive variants and/or fragments thereof described herein or in the following U.S. patents and patent applications: U.S. Pat. Nos. 5,858,363, 6,197,299, 6,514,498, 6,713,284, 6,692,746, 6,632,640, 6,632,441, 6,447,777, 6,399,332, 6,340,461, 6,338,845, 6,251,385, 6,221,351, 6,180,097, 6,126,945, 6,042,837, 6,713,284, 6,632,640, 6,632,441, 5,859,207, 5,728,388, 5,545,716, 5,519,114, 6,926,694, 7,125,554, 7,226,595, 7,226,601, 7,094,603, 7,087,235, 6,835,818, 7,198,398, 6,774,218, 6,913,755, 6,969,616, and 6,713,284, U.S. Patent Application Nos. 2003/0157113, 2003/0124142, 2002/0177551, 2002/0141981, 2002/0115190, 2002/0051765, and 2001/0046501, and PCT International Publication Number WO/03/094846.

As used herein, the term "targeting moiety" refers to any structure, molecule or moiety that is able to bind to a cellular molecule, for example, a cell surface molecule, preferably a disease specific molecule such as an antigen expressed preferentially on a cancer (or cancerous) cell. Exemplary targeting moieties include, but are not limited to, antibodies (including antigen binding fragments thereof) and the like, soluble T-cell receptors, interleukins, hormones, and growth factors.

As used herein, the terms "tumor-targeted superantigen" or "TTS" or "cancer-targeted superantigen" are understood to mean a molecule comprising one or more superantigens covalently linked (either directly or indirectly) with one or more targeting moieties.

As used herein, the term "T-cell receptor" is understood to mean a receptor that is specific to T-cells, and includes the understanding of the term as known in the art. The term also includes, for example, a receptor that comprises a disulfide-linked heterodimer of the highly variable α or β chains expressed at the cell membrane as a complex with the invariant CD3 chains, and a receptor made up of variable γ and δ chains expressed at the cell membrane as a complex with CD3 on a subset of T-cells.

As used herein, the terms "therapeutically effective amount" and "effective amount," are understood to mean an amount of an active agent, for example, a pharmaceutically active agent or a pharmaceutical composition that produces at least some effect in treating a disease or a condition. The effective amount of pharmaceutically active agent(s) used to practice the present invention for a therapeutic treatment varies depending upon the manner of administration, the age, body weight, and general health of the subject. These terms include, but are not limited to synergistic situations such as those described in the instant invention wherein a single agent alone, such as a superantigen conjugate or an immunopotentiator (for example, an anti-PD-1 antibody), may act weakly or not at all, but when combined with each other, for example, but not limited to, via sequential dosage, the two or more agents act to produce a synergistic result.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

As used herein, the terms "treat," "treating" and "treatment" are understood to mean the treatment of a disease in a mammal, e.g., in a human. This includes: (a) inhibiting the disease, i.e., arresting its development; and (b) relieving the disease, i.e., causing regression of the disease state; and (c) curing the disease. As used in the context of a therapeutic treatment, the terms "prevent" or "block" are understood to completely prevent or block, or not completely prevent or block (e.g., partially prevent or block) a given act, action, activity, or event.

As used herein, the term "inhibits the growth of a cancer" is understood to mean a measurably slowing, stopping, or reversing the growth rate of the cancer or cancerous cells in vitro or in vivo. Desirably, the growth rate is slowed by 20%, 30%, 50%, or 70% or more, as determined using a suitable assay for determination of cell growth rates. Typically, a reversal of growth rate is accomplished by initiating or accelerating necrotic or apoptotic mechanisms of cell death in neoplastic cells, resulting in a shrinkage of a neoplasm.

As used herein, the terms "variant," "variants," "modified," "altered," "mutated," and the like, are understood to mean proteins or peptides and/or other agents and/or compounds that differ from a reference protein, peptide or other compound. Variants in this sense are described below and elsewhere in greater detail. For example, changes in a nucleic acid sequence of the variant may be silent, e.g., they may not alter the amino acids encoded by the nucleic acid sequence. Where alterations are limited to silent changes of this type a variant will encode a peptide with the same amino acid sequence as the reference peptide. Changes in the nucleic acid sequence of the variant may alter the amino acid sequence of a peptide encoded by the reference nucleic acid sequence. Such nucleic acid changes may result in amino acid substitutions, additions, deletions, fusions and/or truncations in the protein or peptide encoded by the reference sequence, as discussed below. Generally, differences in amino acid sequences are limited so that the sequences of the reference and the variant are similar overall and, in many regions, identical. A variant and reference protein or peptide may differ in amino acid sequence by one or more substitutions, additions, deletions, fusions and/or truncations, which may be present in any combination. A variant may also be a fragment of a protein or peptide of the invention that differs from a reference protein or peptide sequence by being shorter than the reference sequence, such as by a terminal or internal deletion. Another variant of a protein or peptide of the invention also includes a protein or peptide which retains essentially the same function or activity as the reference protein or peptide. A variant may also be: (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature protein or peptide is fused with another compound, such as a compound to increase the half-life of the protein or peptide (for example, polyethylene glycol), or (iv) one in which the additional amino acids are fused to the mature protein or peptide, such as a leader or secretory sequence or a sequence which is employed for purification of the mature protein or peptide. Variants may be made by mutagenesis techniques, and/or altering mechanisms such as chemical alterations, fusions, adjuncts and the like, including those applied to nucleic acids, amino acids, cells or organisms, and/or may be made by recombinant means.

As used herein, the term "sequential dosage" and related terminology refers to the administration of at least one superantigen, with at least one immunopotentiator, and includes staggered doses of these agents (i.e., time-staggered) and variations in dosage amounts. This includes one agent being administered before, overlapping with (partially or totally), or after administration of another agent. This term generally considers the best administration scheme to achieve a synergistic combination of at least one superantigen and at least one immunopotentiator. By such a dosing strategy (e.g., a sequential dosage), one may be able to achieve synergistic effects of combined superantigen and immunopotentiator administration. In addition, the term "sequential dosage" and related terminology also includes the administration of at least one superantigen, one immunopotentiator and more or more optional additional compounds such as, for example, a corticosteroid, an immune modulator, and another agent designed to reduce potential immunoreactivity to the superantigen conjugate administered to the subject.

As used herein, the terms "systemic" and "systemically" in the context of administration are understood to mean administration of an agent such that the agent is exposed to at least one system associated with the whole body, such as but not limited to the circulatory system, immune system, and lymphatic system, rather than only to a localized part of the body, such as but not limited to within a tumor. Thus, for example, a systemic therapy or an agent administered systematically is a therapy or an agent in which at least one system associated with the entire body is exposed to the therapy or agent, as opposed to, rather than just a target tissue.

As used herein, the term "parenteral administration" includes any form of administration in which the compound is absorbed into the subject without involving absorption via the intestines. Exemplary parenteral administrations that are used in the present invention include, but are not limited to intramuscular, intravenous, intraperitoneal, or intraarticular administration.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

At various places in the present specification, values are disclosed in groups or in ranges. It is specifically intended that the description include each and every individual sub-combination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing and method steps.

Further, it should be understood that elements and/or features of a composition or a method described herein can be combined in a variety of ways without departing from the spirit and scope of the present invention, whether explicit or implicit herein. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features and depicted herein can be applicable to all aspects of the invention(s) described and depicted herein.

II. Superantigen Conjugate

A. Superantigens

Superantigens are bacterial proteins, viral proteins, and human-engineered proteins, capable of activating T lymphocytes, for example, at picomolar concentrations. Superantigens can also activate large subsets of T lymphocytes (T-cells). Superantigens can bind to the major histocompatibility complex I (MHCI) without being processed and, in particular, can bind to conserved regions outside the antigen-binding groove on MEW class II molecules, avoiding most of the polymorphism in the conventional peptide-binding site. Superantigens can also bind to the Vβ chain of the T-cell receptor (TCR) rather than binding to the hypervariable loops of the T-cell receptor. Examples of bacterial superantigens include, but are not limited to, Staphylococcal enterotoxin (SE), *Streptococcus pyogenes* exotoxin (SPE), *Staphylococcus aureus* toxic shock-syndrome toxin (TSST-1), Streptococcal mitogenic exotoxin (SME), Streptococcal superantigen (SSA), Staphylococcal enterotoxin A (SEA), Staphylococcal enterotoxin A (SEB), and Staphylococcal enterotoxin E (SEE).

The polynucleotide sequences encoding many superantigens have been isolated and cloned and superantigens expressed from these or modified (reengineered) polynucleotide sequences have been used in anti-cancer therapy (see, naptumomab estafenatox/ANYARA®, discussed below). Superantigens expressed by these polynucleotide sequences may be wild-type superantigens, modified superantigens, or wild-type or modified superantigens conjugated or fused with targeting moieties. The superantigens may be administered to a mammal, such as a human, directly, for example by injection, or may be delivered, for example, by exposure of blood of a patient to the superantigen outside the body, or, for example, via placing a gene encoding a superantigen inside a mammal to be treated (e.g., via known gene therapy methods and vectors such as, for example, via cells containing, and capable of expressing, the gene) and expressing the gene within the mammal.

Examples of superantigens and their administration to mammals are described in the following U.S. patents and patent applications: U.S. Pat. Nos. 5,858,363, 6,197,299, 6,514,498, 6,713,284, 6,692,746, 6,632,640, 6,632,441, 6,447,777, 6,399,332, 6,340,461, 6,338,845, 6,251,385, 6,221,351, 6,180,097, 6,126,945, 6,042,837, 6,713,284, 6,632,640, 6,632,441, 5,859,207, 5,728,388, 5,545,716, 5,519,114, 6,926,694, 7,125,554, 7,226,595, 7,226,601, 7,094,603, 7,087,235, 6,835,818, 7,198,398, 6,774,218, 6,913,755, 6,969,616, and 6,713,284, U.S. Patent Application Nos. 2003/0157113, 2003/0124142, 2002/0177551, 2002/0141981, 2002/0115190, and 2002/0051765, and PCT International Publication Number WO/03/094846.

B. Modified Superantigens

Within the scope of this invention, superantigens may be engineered in a variety of ways, including modifications that retain or enhance the ability of a superantigen to stimulate T lymphocytes, and may, for example, alter other aspects of the superantigen, such as, for example, its seroreactivity or immunogenicity. Modified superantigens include synthetic molecules that have superantigen activity (i.e., the ability to activate subsets of T lymphocytes).

It is contemplated that various changes may be made to the polynucleotide sequences encoding a superantigen without appreciable loss of its biological utility or activity, namely the induction of the T-cell response to result in cytotoxicity of the tumor cells. Furthermore, the affinity of the superantigen for the MHC class II molecule can be decreased with minimal effects on the cytotoxicity of the superantigen. This, for example, can help to reduce toxicity that may otherwise occur if a superantigen retains its wild-type ability to bind MHC class II antigens (as in such a case, class II expressing cells, such as immune system cells, could also be affected by the response to the superantigen).

Techniques for modifying superantigens (e.g., polynucleotides and polypeptides), including for making synthetic superantigens, are well known in the art and include, for example PCR mutagenesis, alanine scanning mutagenesis, and site-specific mutagenesis (see, U.S. Pat. Nos. 5,220,007; 5,284,760; 5,354,670; 5,366,878; 5,389,514; 5,635,377; and 5,789,166).

In some embodiments, a superantigen may be modified such that its seroreactivity is reduced compared to a reference wild-type superantigen, but its ability to activate T-cells is retained or enhanced relative to wild-type. One technique for making such modified superantigens includes substituting certain amino acids in certain regions from one superantigen to another. This is possible because many superantigens, including but not limited to, SEA, SEE, and SED, share sequence homology in certain areas that have been linked to certain functions (Marrack and Kappler (1990) SCIENCE 248(4959): 1066; see also FIG. 2, which shows region of homology between different wild type and engineered superantigens). For example, in certain embodiments of the present invention, a superantigen that has a desired T-cell activation-inducing response, but a non-desired high seroreactivity, is modified such that the resulting superantigen retains its T-cell activation ability but has reduced seroreactivity.

It is known and understood by those of skill in the art that the sera of humans normally contain various titers of antibodies against superantigens. For the staphylococcal superantigens, for instance, the relative titers are TSST-1>SEB>SEC-1>SE3>SEC2>SEA>SED>SEE. As a result, the seroreactivity of, for example, SEE (Staphylococcal enterotoxin E) is lower than that of, for example, SEA (Staphylococcal enterotoxin A). Based on this data, one skilled in the art may prefer to administer a low titer superantigen, such as, for example SEE, instead of a high titer superantigen, such as, for example, SEB (Staphylococcal enterotoxin B). However, as has also been discovered, different superantigens have differing T-cell activation properties relative to one another, and for wild-type superantigens, the best T-cell activating superantigens often also have undesirably high seroreactivity.

These relative titers sometimes correspond to potential problems with seroreactivity, such as problems with neutralizing antibodies. Thus, the use of a low titer superantigen, such as SEA or SEE may be helpful in reducing or avoiding seroreactivity of parenterally administered superantigens. A low titer superantigen has a low seroreactivity as measured, for example, by typical anti-superantigen antibodies in a general population. In some instances it may also have a low immunogenicity. Such low titer superantigens may be modified to retain its low titer as described herein.

Approaches for modifying superantigens can be used to create superantigens that have both the desired T-cell activation properties and reduced seroreactivity, and in some instances also reduced immunogenicity. Given that certain regions of homology between superantigens relate to seroreactivity, it is possible to engineer a recombinant superantigen that has a desired T-cell activation and a desired seroreactivity and/or immunogenicity. Furthermore, the protein sequences and immunological cross-reactivity of the superantigens or staphylococcal enterotoxins are divided into two related groups. One group consists of SEA, SEE and SED.

The second group is SPEA, SEC and SEB. Thus, it is possible to select low titer superantigens to decrease or eliminate the cross-reactivity with high titer or endogenous antibodies directed against staphylococcal enterotoxins.

Regions in the superantigens that are believed to play a role in seroreactivity include, for example, Region A, which comprises amino acid residues 20, 21, 22, 23, 24, 25, 26, and 27; Region B, which comprises amino acid residues 34, 35, 36, 37, 38, 39, 40, 41, 42, 43, 44, 45, 46, 47, 48, and 49; Region C, which comprises amino acid residues 74, 75, 76, 77, 78, 79, 80, 81, 82, 83, and 84; Region D, which comprises amino acid residues 187, 188, 189 and 190; and Region E, which comprise the amino acid residues, 217, 218, 219, 220, 221, 222, 223, 224, 225, 226, and 227 (see, U.S. Pat. No. 7,125,554, and FIG. 2 herein). Thus, it is contemplated that these regions can be mutated using, for example amino acid substitution, to produce a superantigen having altered seroreactivity.

Polypeptide or amino acid sequences for the above listed superantigens can be obtained from any sequence data bank, for example Protein Data Bank and/or GenBank. Exemplary GenBank accession numbers include, but are not limited to, SEE is P12993; SEA is P013163; SEB is P01552; SEC1 is P01553; SED is P20723; and SEH is AAA19777.

In certain embodiments of the present invention, the wild-type SEE sequence (SEQ ID NO: 1) or the wild type SEA sequence (SEQ ID NO: 2) can be modified such that amino acids in any of the identified regions A-E (see, FIG. 2) are substituted with other amino acids. Such substitutions include for example, K79, K81, K83 and D227 or K79, K81, K83, K84 and D227, or, for example, K79E, K81E, K83S and D227S or K79E, K81E, K83S, K84S and D227A. In certain embodiments, the superantigen is SEA/E-120 (SEQ ID NO: 3; see also U.S. Pat. No. 7,125,554) or SEA$_{D227A}$ (SEQ ID NO: 4; see also U.S. Pat. No. 7,226,601).

1. Modified Polynucleotides and Polypeptides

A biological functional equivalent of a polynucleotide encoding a naturally occurring or a reference superantigen may comprise a polynucleotide that has been engineered to contain distinct sequences while at the same time retaining the capacity to encode the naturally occurring or reference superantigen. This can be accomplished due to the degeneracy of the genetic code, i.e., the presence of multiple codons, which encode for the same amino acids. In one example, it is possible to introduce a restriction enzyme recognition sequence into a polynucleotide while not disturbing the ability of that polynucleotide to encode a protein. Other polynucleotide sequences may encode superantigens that are different but functionally substantially equivalent in at least one biological property or activity (for example, at least 50%, 60%, 70%, 80%, 90%, 95%, 98% of the biological property or activity, for example, without limitation, the ability to induce a T-cell response that results in cytotoxicity of the tumor cells) to a reference superantigen.

In another example, a polynucleotide may be (and encode) a superantigen functionally equivalent to a reference superantigen even though it may contain more significant changes. Certain amino acids may be substituted for other amino acids in a protein structure without appreciable loss of interactive binding capacity with structures such as, for example, antigen-binding regions of antibodies, binding sites on substrate molecules, receptors, and such like. Furthermore, conservative amino acid replacements may not disrupt the biological activity of the protein, as the resultant structural change often is not one that impacts the ability of the protein to carry out its designed function. It is thus contemplated that various changes may be made in the sequence of genes and proteins disclosed herein, while still fulfilling the goals of the present invention.

Amino acid substitutions may be designed to take advantage of the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents. In addition, it may be possible to introduce non-naturally occurring amino acids. Approaches for making amino acid substitutions with other naturally occurring and non-naturally occurring amino acid are described in U.S. Pat. No. 7,763,253.

In terms of functional equivalents, it is understood that, implicit in the definition of a "biologically functional equivalent" protein and/or polynucleotide, is the concept that there is a limited number of changes that may be made within a defined portion of the molecule while retaining a molecule with an acceptable level of equivalent biological activity. Biologically functional equivalents are thus considered to be those proteins (and polynucleotides) where selected amino acids (or codons) may be substituted without substantially affecting biological function. Functional activity includes the induction of the T-cell response to result in cytotoxicity of the tumor cells.

In addition, it is contemplated that a modified superantigen can be created by substituting homologous regions of various proteins via "domain swapping," which involves the generation of chimeric molecules using different but, in this case, related polypeptides. By comparing various superantigen proteins to identify functionally related regions of these molecules (see, e.g., FIG. 2), it is possible to swap related domains of these molecules so as to determine the criticality of these regions to superantigen function. These molecules may have additional value in that these "chimeras" can be distinguished from natural molecules, while possibly providing the same function.

In certain embodiments, the superantigen comprises an amino acid sequence that is at least 70%, 75%, 80%, 85%, 90%, 95%, 98%, or 99% identical to the sequence of a reference superantigen selected from the group consisting of SEQ ID NO: 1, SEQ ID NO: 2, SEQ ID NO: 3, and SEQ ID NO: 4, wherein the superantigen optionally retains at least 50%, 60%, 70% 80%, 90%, 95%. 98%, 99%, or 100% of a biological activity or property of the reference superantigen.

In certain embodiments, the superantigen comprises an amino acid sequence that is encoded by a nucleic acid that is at least 70%, 75%, 80%, 85%, 90%, 95%, 98%, or 99% identical to a nucleic acid encoding the superantigen selected from the group consisting of SEQ ID NO: 1, SEQ ID NO: 2, SEQ ID NO: 3, and SEQ ID NO: 4, wherein the superantigen optionally retains at least 50%, 60%, 70% 80%, 90%, 95%. 98%, 99%, or 100% of a biological activity or property of the reference superantigen.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36, 290-300; Altschul et al., (1997) Nucleic Acids Res. 25:3389-3402, incorporated by reference) are tailored for sequence similarity searching. For a discussion of basic issues in searching sequence databases see Altschul et al., (1994) Nature Genetics 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; −W, wordsize [Integer]: default=11 for nucleotides/28 for megablast/3 for proteins; −y, Dropoff (X) for blast extensions in bits: default=20 for blastn/7 for others; −X, X dropoff value for gapped alignment (in bits): default=15 for all programs, not applicable to blastn; and −Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

C. Targeted Superantigens

In order to increase specificity, the superantigen preferably is conjugated to a targeting moiety to create a targeted superantigen conjugate that binds an antigen preferentially expressed by a cancer cell, for example, a cell surface antigen such as 5T4. The targeting moiety is a vehicle that can be used to bind superantigen to the cancerous cells, for example, the surface of the cancerous cells. The targeted superantigen conjugate should retain the ability to activate large numbers of T lymphocytes. For example, the targeted superantigen conjugate should activate large numbers of T-cells and direct them to tissues containing the tumor-associated antigen bound to the targeting moiety. In such situations, specific target cells are preferentially killed, leaving the rest of the body relatively unharmed. This type of therapy is desirable, as non-specific anti-cancer agents, such as cytostatic chemotherapeutic drugs, are nonspecific and kill large numbers of cells not associated with tumors to be treated. For example, studies with targeted superantigen conjugates have shown that inflammation with infiltration by cytotoxic T lymphocytes (CTLs) into tumor tissue increases rapidly in response to the first injection of a targeted superantigen (Dohlsten et al. (1995) Proc. Natl.

ACAD. SCI. USA 92:9791-9795). This inflammation with infiltration of CTLs into the tumor is one of the major effectors of the anti-tumor therapeutic of targeted superantigens.

Tumor-targeted superantigens represent an immunotherapy against cancer and are therapeutic fusion proteins containing a targeting moiety conjugated to a superantigen (Dohlsten et al. (1991) PROC. NATL. ACAD. SCI. USA 88:9287-9291; Dohlsten et al. (1994) PROC. NATL. ACAD. SCI. USA 91:8945-8949).

The targeting moiety can in principle be any structure that is able to bind to a cellular molecule, for example, a cell surface molecule and preferably is a disease specific molecule. The targeted molecule (e.g., antigen) against which the targeting moiety is directed is usually different from (a) the Vβ chain epitope to which superantigen binds, and (b) the MHC class II epitopes to which superantigens bind. The targeting moiety can be selected from antibodies, including antigen binding fragments thereof, soluble T-cell receptors, growth factors, interleukins (e.g., interleukin-2), hormones, etc.

In certain preferred embodiments, the targeting moiety is an antibody (e.g., Fab, F(ab)$_2$, Fv, single chain antibody, etc.). Antibodies are extremely versatile and useful cell-specific targeting moieties because they typically can be generated against any cell surface antigen of interest. Monoclonal antibodies have been generated against cell surface receptors, tumor-associated antigens, and leukocyte lineage-specific markers such as CD antigens. Antibody variable region genes can be readily isolated from hybridoma cells by methods well known in the art. Exemplary tumor-associated antigens that can be used to produce a targeting moiety can include, but are not limited to gp100, Melan-A/MART, MAGE-A, MAGE (melanoma antigen E), MAGE-3, MAGE-4, MAGEA3, tyrosinase, TRP2, NY-ESO-1, CEA (carcinoembryonic antigen), PSA, p53, Mammaglobin-A, Survivin, Muc1(mucin1)/DF3, metallopanstimulin-1 (MPS-1), Cytochrome P450 isoform 1B1, 90K/Mac-2 binding protein, Ep-CAM (MK-1), HSP-70, hTERT (TRT), LEA, LAGE-1/CAMEL, TAGE-1, GAGE, 5T4, gp70, SCP-1, c-myc, cyclin B1, MDM2, p62, Koc, IMP1, RCAS1, TA90, 0A1, CT-7, HOM-MEL-40/SSX-2, SSX-1, SSX-4, HOM-TES-14/SCP-1, HOM-TES-85, HDACS, MBD2, TRIP4, NY--CO-45, KNSL6, HIP1R, Seb4D, KIAA1416, IMP1, 90K/Mac-2 binding protein, MDM2, NY/ESO, and LMNA.

Exemplary cancer-targeting antibodies can include, but are not limited to, anti-CD19 antibodies, anti-CD20 antibodies, anti-5T4 antibodies, anti-Ep-CAM antibodies, anti-Her-2/neu antibodies, anti-EGFR antibodies, anti-CEA antibodies, anti-prostate specific membrane antigen (PSMA) antibodies, and anti-IGF-1R antibodies. It is understood that the superantigen can be conjugated to an immunologically reactive antibody fragment such as C215Fab, 5T4Fab (see, WO8907947) or C242Fab (see, WO9301303).

Examples of tumor targeted superantigens that can be used in the present invention include C215Fab-SEA (SEQ ID NO: 5), 5T4Fab-SEA$_{D227A}$ (SEQ ID NO: 6) and 5T4Fab-SEA/E-120 (SEQ ID NO: 7, see FIG. 3).

In a preferred embodiment, a preferred conjugate is a superantigen conjugate known as Naptumomab estafenatox/ANYARA®, which is the fusion protein of the Fab fragment of an anti-5T4 antibody and the SEA/E-120 superantigen. Naptumomab estafenatox/ANYARA® comprises two protein chains that cumulatively include an engineered Staphylococcal enterotoxin superantigen (SEA/E-120) and a targeting 5T4 Fab comprising modified 5T4 variable region sequences fused to the constant region sequences of the murine IgG1/κ antibody C242. The first protein chain comprises residues 1 to 458 of SEQ ID NO: 7 (see also, SEQ ID NO: 8), and includes a chimeric 5T4 Fab heavy chain, corresponding to residues 1 to 222 of SEQ ID NO: 7, and the SEA/E-120 superantigen, corresponding to residues 226 to 458 of SEQ ID NO: 7, covalently linked via a GGP tripeptide linker, corresponding to residues 223-225 of SEQ ID NO: 7. The second chain comprises residues 459 to 672 of SEQ ID NO: 7 (see also, SEQ ID NO: 9) and includes a chimeric 5T4 Fab light chain. The two protein chains are held together by non-covalent interactions between the Fab heavy and light chains. Residues 1-458 of SEQ ID NO: 7 correspond to residues 1-458 of SEQ ID NO: 8, and residues 459-672 of SEQ ID NO: 7 correspond to residues 1-214 of SEQ ID NO: 9. Naptumomab estafenatox/ANYARA® comprises the proteins of SEQ ID NOS: 8 and 9 held together by non-covalent interactions between the Fab heavy and Fab light chains. Naptumomab estafenatox/ANYARA® induces T-cell mediated killing of cancer cells at concentrations around 10 pM and the superantigen component of the conjugate has been engineered to have low binding to human antibodies and MHC Class II.

It is contemplated that other antibody based targeting moieties can be designed, modified, expressed, and purified using techniques known in the art and discussed in more detail below.

Another type of targeting moiety includes a soluble T-cell receptor (TCR). Some forms of soluble TCR may contain either only extracellular domains or extracellular and cytoplasmic domains. Other modifications of the TCR may also be envisioned to produce a soluble TCR in which the transmembrane domains have been deleted and/or altered such that the TCR is not membrane bound as described in U.S. Publication Application Nos. U.S. 2002/119149, U.S. 2002/0142389, U.S. 2003/0144474, and U.S. 2003/0175212, and International Publication Nos. WO2003020763; WO9960120 and WO9960119.

The targeting moiety can be conjugated to the superantigen by using either recombinant techniques or chemically linking of the targeting moiety to the superantigen.

1. Recombinant Linker (Fusion Protein)

It is contemplated that a gene encoding a superantigen linked directly or indirectly (for example, via an amino acid containing linker) to a targeting moiety can be created and expressed using conventional recombinant DNA technologies. For example, the amino terminal of a modified superantigen can be linked to the carboxy terminal of a targeting moiety or vice versa. For antibodies, or antibody fragments that may serve as targeting moieties, either the light or the heavy chain may be utilized for creating a fusion protein. For example, for a Fab fragment, the amino terminus of the modified superantigen can be linked to the first constant domain of the heavy antibody chain (CH$_1$). In some instances, the modified superantigen can be linked to a Fab fragment by linking the VH and VL domain to the superantigen. Alternatively, a peptide linker can be used to join the superantigen and targeting moiety together. When a linker is employed, the linker preferably contains hydrophilic amino acid residues, such as Gln, Ser, Gly, Glu, Pro, His and Arg. Preferred linkers are peptide bridges consisting of 1-10 amino acid residues, more particularly, 3-7 amino acid residues. An exemplary linker is the tripeptide -GlyGlyPro-. These approaches have been used successfully in the design and manufacture of the naptumomab estafenatox/ANYARA® superantigen conjugate.

2. Chemical Linkage

It is also contemplated that the superantigen may be linked to the targeting moiety via a chemical linkage.

Chemical linkage of the superantigen to the targeting moiety may require a linker, for example, a peptide linker. The peptide linker preferably is hydrophilic and exhibits one or more reactive moieties selected from amides, thioethers, disulfides etc. (See, U.S. Pat. Nos. 5,858,363, 6,197,299, and 6,514,498). It is also contemplated that the chemical linkage can use homo- or heterobifunctional crosslinking reagents. Chemical linking of a superantigen to a targeting moiety often utilizes functional groups (e.g., primary amino groups or carboxy groups) that are present in many positions in the compounds.

D. Expression of Superantigens and Superantigen Conjugates

When recombinant DNA technologies are employed, the superantigen or the superantigen-targeting moiety conjugate may be expressed using standard expression vectors and expression systems. The expression vectors, which have been genetically engineered to contain the nucleic acid sequence encoding the superantigen, are introduced (e.g., transfected) into host cells to produce the superantigen (see, e.g. Dohlsten et al. (1994), Forsberg et al. (1997) J. BIOL. CHEM. 272:12430-12436, Erlandsson et al. (2003) J. MOL. BIOL. 333:893-905 and WO2003002143).

Host cells can be genetically engineered, for example, by transformation or transfection technologies, to incorporate nucleic acid sequences and express the superantigen. Introduction of nucleic acid sequences into the host cell can be affected by calcium phosphate transfection, DEAE-dextran mediated transfection, microinjection, cationic lipid-mediated transfection, electroporation, transduction, scrape loading, ballistic introduction, infection or other methods. Such methods are described in many standard laboratory manuals, such as, Davis et al. (1986) BASIC METHODS IN MOLECULAR BIOLOGY and Sambrook, et al. (1989) MOLECULAR CLONING: A LABORATORY MANUAL, 2nd Ed., Cold Spring Harbor Laboratory Press, Cold Spring Harbor, N.Y.

Representative examples of appropriate host cells include bacterial cells, such as streptococci, staphylococci, *E. coli*, *Streptomyces* and *Bacillus subtilis* cells; fungal cells, such as yeast cells and aspergillus cells; insect cells such as Drosophila S2 and Spodoptera Sf9 cells; animal cells such as CHO, COS, HeLa, C127, 3T3, BHK, 293 and Bowes melanoma cells.

Examples of production systems for superantigens are found, for example, in U.S. Pat. No. 6,962,694.

E. Protein Purification

The superantigen and/or the superantigen-targeting moiety conjugates preferably are purified prior to use, which can be accomplished using a variety of purification protocols. Having separated the superantigen or the superantigen-targeting moiety conjugate from other proteins, the protein of interest may be further purified using chromatographic and electrophoretic techniques to achieve partial or complete purification (or purification to homogeneity). Analytical methods particularly suited to the preparation of a pure peptide are ion-exchange chromatography, size exclusion chromatography; affinity chromatography; polyacrylamide gel electrophoresis; isoelectric focusing. The term "purified" as used herein, is intended to refer to a composition, isolatable from other components, wherein the macromolecule (e.g., protein) of interest is purified to any degree relative to its original state. Generally, the terms "purified" refer to a macromolecule that has been subjected to fractionation to remove various other components, and which substantially retains its biological activity. The term "substantially purified" refers to a composition in which the macromolecule of interest forms the major component of the composition, such as constituting about 50%, about 60%, about 70%, about 80%, about 90%, about 95% or more of the content of the composition.

Various methods for quantifying the degree of purification of the protein are known to those of skill in the art, including, for example, determining the specific activity of an active fraction, and assessing the amount of a given protein within a fraction by SDS-PAGE analysis, High Performance Liquid Chromatography (HPLC), or any other fractionation technique. Various techniques suitable for use in protein purification include, for example, precipitation with ammonium sulfate, PEG, antibodies and the like or by heat denaturation, followed by centrifugation; chromatography steps such as ion exchange, gel filtration, reverse phase, hydroxyapatite, affinity chromatography; isoelectric focusing; gel electrophoresis; and combinations of such and other techniques. It is contemplated that the order of conducting the various purification steps may be changed, or that certain steps may be omitted, and still result in a suitable method for the preparation of a substantially purified protein or peptide.

III. Immunopotentiator

It is contemplated that the efficacy of the immunopotentiator can be enhanced by administering the immunopotentiator to the subject to be treated together with a superantigen conjugate comprising the superantigen and the targeting moiety. Exemplary immunopotentiators can, for example: (a) stimulate activating T-cell signaling, (b) repress T-cell inhibitory signalling between the cancerous cells and a T-cell, (c) repress inhibitory signalling that leads to T-cell expansion, activation and/or activity via a non-human IgG1-mediated immune response pathway, for example, a human IgG4 immunoglobulin-mediated pathway, (d) a combination of (a) and (b), (e) combination of (a) and (c), (f) a combination of (b) and (c), and (g) a combination of (a), (b), and (c).

In certain embodiments the immunopotentiator is a checkpoint pathway inhibitor. A number of T-cell checkpoint inhibitor pathways have been identified to date, for example, the PD-1 immune checkpoint pathway and Cytotoxic T-lymphocyte antigen-4 (CTLA-4) immune checkpoint pathway.

Sundstedt et al. (Sundstedt et al. (2012) J. IMMUNOTHER. 35:344-35), showed that a combination of a tumor targeted superantigen (TTS) with an anti-CTLA4 IgG1 antibody in a mouse B16 melanoma model was more active than the individual components. In that study, although the superantigen caused infiltration of both CD4+ and CD8+ T-cells, a large number of regulatory T-cells (Tregs) accumulated in the tumor microenvironment as well. The upregulation of these suppressive regulatory cells is believed to be a direct consequence of TTS therapy, which may limit its effectiveness. The authors noted that it was likely that the extreme upregulation of CTLA-4 by the TTS led to the effect of the anti-CTLA-4 antibody mainly being on the Treg population. Without wishing to be bound by theory, it is contemplated that the CTLA-4 IgG1 antibody is cytotoxic to the Treg population, which is central to its anti-cancer activity when used in combination with a TTS. In contrast, certain embodiments of the present invention use antibodies not known to deplete Tregs, e.g., IgG4 antibodies directed at non-CTLA-4 checkpoints (for example, anti-PD-1 IgG4 inhibitors), and therefore represent a novel combination whose synergistic effects are mediated by other mechanisms of action.

PD-1 is a receptor present on the surface of T-cells that serves as an immune system checkpoint that inhibits or otherwise modulates T-cell activity at the appropriate time to prevent an overactive immune response. Cancer cells, however, can take advantage of this checkpoint by expressing ligands, for example, PD-L1, PD-L2, etc., that interact with PD-1 on the surface of T-cells to shut down or modulate T-cell activity. Using this approach, cancer can evade the T-cell mediated immune response.

In the CTLA-4 pathway, the interaction of CTLA-4 on the T-cell with its ligands (e.g., CD80, also known as B7-1, and CD86) on the surface of an antigen presenting cells (rather than the cancer calls) leads to T-cell inhibition. As a result, the ligand that inhibits T-cell activation or activity (e.g., CD80 or CD86) is provided by an antigen presenting cell (a key cell type in the immune system) rather than the cancer cell. Although CTLA-4 and PD-1 binding both have similar negative effects on T-cells the timing of downregulation, the responsible signaling mechanisms, and the anatomic locations of immune inhibition by these two immune checkpoints differ (American Journal of Clinical Oncology. Volume 39, Number 1, February 2016). Unlike CTLA-4, which is confined to the early priming phase of T-cell activation, PD-1 functions much later during the effector phase, (Keir et al. (2008) ANNU. REV IMMUNOL., 26:677-704). Consequently, T-cell inhibition mediated via the PD-1 checkpoint pathway is very different from T-cell inhibition mediated via the CTLA-4 checkpoint pathway.

In certain embodiments, the immunopotentiator prevents (completely or partially) an antigen expressed by the cancerous cell from repressing T-cell inhibitory signaling between the cancerous cell and the T-cell. In one embodiment, such an immunopotentiator is a checkpoint inhibitor, for example, a PD-1 inhibitor. Examples of such immunopotentiators include, for example, anti-PD-1 antibodies, anti-PD-L1 antibodies, and anti-PD-L2 antibodies. Accordingly, in one embodiment the superantigen conjugate is administered with a PD-1-based immunopotentiator, which can include (1) a molecule (for example, an antibody or small molecule) that binds to a PD-1 ligand (for example, PD-L1 or PD-L2) to prevent the PD-1 ligand from binding to its cognate PD-1 on the T-cell, and/or (2) a molecule (for example, an antibody or small molecule) that binds to PD-1 on a T-cell to prevent the binding of a PD-ligand expressed by the cancer cell of interest.

Furthermore, in certain embodiments, the immunopotentiator prevents (completely or partially) an antigen expressed by the cancerous cell from repressing T-cell expansion, activation and/or activity via a human IgG4 (a non-human IgG1) mediated immune response pathway, for example, not via an ADCC pathway. It is contemplated that, although the immune response potentiated by the superantigen conjugate and the immunopotentiator may include some ADCC activity, the principal component(s) of the immune response do not involve ADCC activity. In contrast, some of the antibodies currently being used in immunotherapy, such as ipilimumab (an anti-CTLA-4 IgG1 monoclonal antibody), can kill targeted cells via ADCC through signaling via their Fc domain through Fc receptors on effector cells. Ipilimumab, like many other therapeutic antibodies, was designed as a human IgG1 immunoglobulin, and although ipilimumab blocks interactions between CTLA-4 and CD80 or CD86, its mechanism of action is believed to include ADCC depletion of tumor-infiltrating regulatory T-cells that express high levels of cell surface CTLA-4. (Mahoney et al. (2015) NATURE REVIEWS, DRUG DISCOVERY 14: 561-584.) Given that CTLA-4 is highly expressed on a subset of T-cells (regulatory T-cells) that act to negatively control T-cells activation, when an anti-CTLA-4 IgG1 antibody is administered, the number of regulatory T-cells is reduced via ADCC.

In certain embodiments, it is desirable to use immunopotentiators whose mode of action is primarily to block the inhibitory signals between the cancer cells and the T-cells without significantly depleting the T-cell populations (for example, permitting the T-cell populations to expand). To achieve this, it is desirable to use an antibody, for example, an anti-PD-1 antibody, an anti-PD-L1 antibody or an anti-PD-L2 antibody, that has or is based on a human IgG4 isotype. Human IgG4 isotype is preferred under certain circumstances because this antibody isotype invokes little or no ADCC activity compared to the human IgG1 isotype (Mahoney et al. (2015) supra). Accordingly, in certain embodiments, the anti-PD-1 antibody, anti-PD-L1 antibody, anti-PD-L2 has or is based on a human IgG4 isotype. As a result, it is not possible to extrapolate potential therapeutic activity of an anti-PD-1 antibody, anti-PD-L1 antibody, or anti-PD-L2 antibody having human IgG4 isotype based upon activity of an antibody having a different isotype, for example, IgG1 isotype, especially if that antibody is directed to a different antigen, for example, CTLA-4, such as an anti-CTLA-4 human IgG1 immunoglobulin. Furthermore, CTLA-4 and PD-1 represent two T-cell-inhibitory receptors with independent, non-redundant mechanisms of action. Despite their shared ability to block T-cell activation, the two proteins have unique structures and impact very different immune responses to cancer cells.

Exemplary PD-1/PD-L1 based immunopotentiators are described in U.S. Pat. Nos. 8,728,474, 8,952,136, and 9,073,994, and EP Patent No. 1537878B1, and include anti-PD-1 antibodies. Exemplary anti-PD-1 antibodies include nivolumab (Bristol-Myers Squibb Co.), pembrolizumab (KEYTRUDA®, Merck & Co.) and Atezolizumab (formerly MPDL3280A), MEDI4736, Avelumab, and PDR001.

The protein based immunopotentiators may be designed, expressed, and purified using techniques known to those skilled in the art, for example, as described hereinabove. The anti-PD-1 antibodies may be designed, expressed, purified, formulated and administered as described in U.S. Pat. Nos. 8,728,474, 8,952,136, and 9,073,994.

Other immunopotentiators (for example, antibodies, and various small molecules) may target signaling pathways involving one or more of the following ligands: B7-H3 (found on prostrate, renal cell, non-small cell lung, pancreatic, gastric, ovarian, colorectal cells, among others); B7-H4 (found on breast, renal cell, ovarian, pancreatic, melanoma cells, among others); HHLA2 (found on breast, lung , thyroid, melanoma, pancreas, ovary, liver, bladder, colon, prostate, kidney cells, among others); galectins (found on non-small cell lung, colorectal, and gastric cells, among others); CD30 (found on Hodgkin lymphoma, large cell lymphoma cells, among others); CD70 (found on non-Hodgkin's lymphoma, renal cells, among others); ICOSL (found on glioblastoma, melanoma cells, among others); and CD155 (found on kidney, prostrate, pancreatic glioblastoma cells, among others). Similarly, other potential immunopotentiators that can be used include, for example, a 4-1BB (CD137) agonist (e.g., the fully human IgG4 anti-CD137 antibody Urelumab/BMS-663513), a LAG3 inhibitor (e.g., the humanized IgG4 anti-LAG3 antibody LAG525, Novartis); an IDO inhibitor (e.g., the small molecule INCB024360, Incyte Corporation), a TGFβ inhibitor (e.g., the small molecule Galunisertib, Eli Lilly) and other receptor or ligands that are found on T-cells and/or tumor cells and that are amenable to pharmaceutical intervention based on agonist/antagonist interactions but not through ADCC.

A. Antibody Production

Methods for producing antibodies are known in the art. For example, DNA molecules encoding light chain variable regions and heavy chain variable regions can be chemically synthesized using the sequences of the CDRs and variable regions of the antibodies of interest, for example, the antibody sequences provided in U.S. Pat. No. 8,952,136 and the hybridoma deposits described in U.S. Pat. No. 9,073,994. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding the antibodies disclosed herein can be incorporated (ligated) into expression vectors, which can be introduced into host cells through conventional transfection or transformation techniques. Exemplary host cells are E. coli cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If a DNA construct encoding an antibody disclosed herein is to be expressed in eukaryotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy and/or light chain to be expressed. In some embodiments, a single expression vector contains both heavy and light chain variable regions to be expressed.

The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A method of producing a polypeptide comprising an immunoglobulin heavy chain variable region or a polypeptide comprising an immunoglobulin light chain variable region may comprise growing (culturing) a host cell transfected with an expression vector under conditions that permits expression of the polypeptide comprising the immunoglobulin heavy chain variable region or the polypeptide comprising the immunoglobulin light chain variable region. The polypeptide comprising a heavy chain variable region or the polypeptide comprising the light chain variable region then may be purified using techniques well known in the art, e.g., affinity tags such as glutathione-S-transferase (GST) and histidine tags.

A method of producing a monoclonal antibody that binds a target protein, for example, PD-1, PD-L1, or PD-L2, or an antigen-binding fragment of the antibody, may comprise growing a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

B. Antibody Modifications

Methods for reducing or eliminating the antigenicity of antibodies and antibody fragments are known in the art. When the antibodies are to be administered to a human, the antibodies preferably are "humanized" to reduce or eliminate antigenicity in humans. Preferably, a humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al. (1984) PROC. NAT. ACAD. SCI. 81:6851-6855, Neuberger et al. (1984) NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-ErbB3 antibody are grafted onto human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988)

NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al. (2002) J. IMMUNOL. 169:1119-1125.

Other methods to reduce immunogenicity include "reshaping," "hyperchimerization," and "veneering/resurfacing." See, e.g., Vaswami et al. (1998) ANNALS OF ALLERGY, ASTHMA, & IMMUNOL. 81:105; Roguska et al. (1996) PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. Nos. 5,766,886; 5,770,196; 5,821,123; and 5,869,619.

Any suitable approach, including any of the above approaches, can be used to reduce or eliminate human immunogenicity of an antibody including the binding moiety component of the superantigen conjugate disclosed herein.

Methods of making multispecific antibodies are known in the art. Multi-specific antibodies include bispecific antibodies. Bispecific antibodies are antibodies that have binding specificities for at least two different epitopes. Exemplary bispecific antibodies bind to two different epitopes of the antigen of interest. Bispecific antibodies can be prepared as full length antibodies or antibody fragments (e.g., F(ab')$_2$ bispecific antibodies and diabodies) as described, for example, in Milstein et al., NATURE 305:537-539 (1983), WO 93/08829, Traunecker et al., EMBO J., 10:3655-3659 (1991), WO 94/04690, Suresh et al. (1986) METHODS IN ENZYMOLOGY 121:210, WO96/27011, Brennan et al. (1985) SCIENCE 229: 81, Shalaby et al. (1992) J. EXP. MED. 175: 217-225, Kostelny et al. (1992) J. IMMUNOL. 148(5):1547-1553, Hollinger et al. (1993) PNAS, 90:6444-6448, Gruber et al. (1994) J. IMMUNOL. 152:5368, Wu et al. (2007) NAT. BIOTECHNOL. 25(11): 1290-1297, U.S. Patent Publication No. 2007/0071675, and Bostrom et al., SCIENCE 323:1640-1644 (2009).

IV. Formulations and Pharmaceutical Compositions

The superantigen conjugate and immunopotentiator can be administered together, sequentially, or intermittently to the subject so as to treat the cancer, for example, to slow the growth rate of cancer cells, reduce the incidence or number of metastases, reduce tumor size, inhibit tumor growth, reduce the blood supply to a tumor or cancer cells, promote an immune response against cancer cells or a tumor, prevent or inhibit the progression of cancer, for example, by at least 40%, 50%, 60%, 70%, 80%, 90%, 95%, 98%, 99%, or 100%. Alternatively, the superantigen conjugate and immunopotentiator can be administered together, sequentially, or intermittently to the subject so as to treat the cancer, for example, to increase the lifespan of a subject with cancer, for example, by 3 months, 6 months, 9 months, 12 months, 1 year, 5 years, or 10 years.

The superantigen conjugate and the immunopotentiator may be formulated separately or together using techniques known to those skilled in the art. For example, for therapeutic use, the superantigen conjugate and/or the immunopotentiator is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing the superantigen and/or the immunopotentiator disclosed herein can be provided in a single dosage form or different dosage forms. The pharmaceutical composition or compositions should be formulated to be compatible with its intended route of administration. Examples of routes of administration are intravenous (IV), intramuscular, intradermal, inhalation, transdermal, topical, transmucosal, and rectal administration. Alternatively, the agents may be administered locally rather than systemically, for example, via injection of the agent or agents directly into the site of action, often in a depot or sustained release formulation.

Useful formulations can be prepared by methods well known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

The combined superantigen conjugate and immunopotentiator of the present invention may be employed alone or in conjunction with other compounds, such as carriers or other therapeutic compounds. Pharmaceutical compositions of the present invention comprise an effective amount of one or more superantigen conjugates and one or more immunopotentiators, for example an anti-PD-1 antibody, and may also contain additional agents, dissolved or dispersed in a pharmaceutically acceptable carrier. The phrases "pharmaceutical" or "pharmacologically acceptable" refer to substances, e.g., compositions, that do not produce an adverse, allergic or other untoward reaction when administered to a mammal, such as, for example, a human. The preparation of a pharmaceutical composition that contains at least one superantigen conjugate and an immunopotentiator will be known to those of skill in the art in light of the present disclosure, and as exemplified by Remington's Pharmaceutical Sciences, 18th Ed. Mack Printing Company, 1990, incorporated herein by reference. Moreover, for human administration, it will be understood that preparations should meet sterility, pyrogenicity, general safety and purity standards as required by FDA Office of Biological Standards.

In a specific embodiment of the invention, the compositions of the invention comprise tumor-targeted superantigen in combination with an immunopotentiator. Such combinations include, for example, any tumor-targeted superantigen and/or immunopotentiator as described herein.

In a specific embodiment of the invention, the tumor-targeted super antigen comprises a bacterial superantigen including, but are not limited to, Staphylococcal enterotoxin (SE), *Streptococcus pyogenes* exotoxin (SPE), *Staphylococcus aureus* toxic shock-syndrome toxin (TSST-1), Streptococcal mitogenic exotoxin (SME), Streptococcal superantigen (SSA), Staphylococcal enterotoxin A (SEA), Staphylococcal enterotoxin B (SEB), and Staphylococcal enterotoxin E (SEE) conjugated to a targeting moiety. In another embodiment of the invention, the compositions comprise tumor-targeted superantigens comprising superantigens with the following Protein Data Bank and/or GenBank accession numbers include, but are not limited to, SEE is P12993; SEA is P013163; SEB is P01552; SEC1 is P01553; SED is P20723; and SEH is AAA19777, as well as variants thereof, conjugated to a targeting moiety.

In certain embodiments, the superantigen conjugate comprises a wild type or engineered superantigen sequence such as, the wild-type SEE sequence (SEQ ID NO: 1) or the wild type SEA sequence (SEQ ID NO: 2), either of which can be modified such that amino acids in any of the identified regions A-E (see, FIG. 2) are substituted with other amino acids. In certain embodiments, the superantigen incorporated in the conjugate is SEA/E-120 (SEQ ID NO: 3) or SEA$_{D227A}$ (SEQ ID NO: 4).

Specific examples of targeting moieties to be conjugated to the superantigens include, for example, any molecule that is able to bind to a cellular molecule and preferably a disease specific molecule such as a cancer cell specific molecule. The targeting moiety can be selected from antibodies, including antigen binding fragments, soluble T-cell receptors, growth factors, interleukins, hormones, etc. Exemplary cancer targeting antibodies can include, but are not limited to, anti-CD19, anti-CD20 antibodies, anti-5T4 antibodies, anti-Ep-CAM antibodies, anti-Her-2/neu antibodies, anti-EGFR antibodies, anti-CEA antibodies, anti-prostate specific membrane antigen (PSMA) antibodies, and anti-IGF-1R antibodies. In one embodiment, the superantigen can be conjugated to an immunologically reactive antibody fragment such as C215Fab, 5T4Fab (see, WO8907947) or C242Fab (see, WO9301303).

Examples of such tumor-targeted superantigens include C215Fab-SEA (SEQ ID NO: 5), 5T4Fab-SEA$_{D227A}$ (SEQ ID NO: 6) and 5T4Fab-SEA/E-120 (SEQ ID NO: 7). In a preferred embodiment, the superantigen conjugate is 5T4 Fab-SEA/E-120, known in the art as Naptumomab estafenatox/ANYARA®, which comprises two polypeptide sequences that together define an Fab fragment of an anti-5T4 antibody, where one of the polypeptide sequences further comprises the SEA/E-120 superantigen namely SEQ ID NO: 8 (chimeric $V_H$ chain of 5T4 Fab coupled by three amino acid linker to SEA/E-120) and SEQ ID NO: 9 (chimeric $V_L$ chain of 5T4 Fab).

In a preferred embodiment, the compositions of the invention comprise the tumor-targeted superantigen 5T4Fab-SEA/E-120, known in the art as naptumomab estafenatox/ANYARA® in combination with a PD-1 inhibitor, such as an anti-PD-1 antibody, for example, nivolumab (Bristol-Myers Squibb Co.), pembrolizumab (KEYTRUDA®, Merck & Co.), MK-3475 (Merck & Co), pidlizumab (CureTech), AMP-224 (AstraZeneca/Medimmune) and AMP-514 (AstraZeneca/Medimmune) or an anti-PD-L1 antibody such as MPDL3280A (Genentech/Roche), MEDI-4736 (AstraZeneca/Medimmune) and MSB0010718C (EMD Serono/Merck KGA).

In a specific embodiment of the invention, the compositions comprise the targeted super antigen naptumomab estafenatox (ANYARA®) in combination with one or more anti-PD-1 antibodies including nivolumab (Bristol-Myers Squibb Co.), pembrolizumab (KEYTRUDA®, Merck & Co.), Atezolizumab (formerly MPDL3280A), MEDI4736, Avelumab, and PDR001.

Formulations or dosage form containing the superantigen conjugate and immunopotentiator may comprise different types of carriers depending on whether they are to be administered in solid, liquid or aerosol form, and whether it need to be sterile for such routes of administration as injection.

Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. Such determinations are known and used by those of skill in the art.

The active agents are administered in an amount or amounts effective to decrease, reduce, inhibit or otherwise abrogate the growth or proliferation of cancer cells, induce apoptosis, inhibit angiogenesis of a cancer or tumor, inhibit metastasis, or induce cytotoxicity in cells. The effective amount of active compound(s) used to practice the present invention for therapeutic treatment of cancer varies depending upon the manner of administration, the age, body weight, and general health of the subject. These terms include synergistic situations such as those presented and described in the instant invention wherein a single agent alone, such as a superantigen conjugate or an immunopotentiator such as an anti-PD-1 antibody, may act weakly or not at all, but when combined with each other, for example, but not limited to, via sequential dosage, the two or more agents act to produce a synergistic result.

In certain non-limiting examples, a dose of the superantigen conjugate may also comprise from about 1 microgram/kg/body weight, about 5 microgram/kg/body weight, about 10 microgram/kg/body weight, about 15 microgram/kg/body weight, about 20 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, about 1 microgram/kg/body weight to about 100 milligram/kg/body weight. Other exemplary dosage ranges, range from about 1 microgram/kg/body weight to about 1000 microgram/kg/body weight, from about 1 microgram/kg/body weight to about 100 microgram/kg/body weight, from about 1 microgram/kg/body weight to about 75 microgram/kg/body weight, from about 1 microgram/kg/body weight to about 50 microgram/kg/body weight, from about 1 microgram/kg/body weight to about 40 microgram/kg/body weight, from about 1 microgram/kg/body weight to about 30 microgram/kg/body weight, from about 1 microgram/kg/body weight to about 20 microgram/kg/body weight, from about 1 microgram/kg/body weight to about 15 microgram/kg/body weight, from about 1 microgram/kg/body weight to about 10 microgram/kg/body weight, from about 5 microgram/kg/body weight to about 1000 microgram/kg/body weight, from about 5 microgram/kg/body weight to about 100 microgram/kg/body weight, from about 5 microgram/kg/body weight to about 75 microgram/kg/body weight, from about 5 microgram/kg/body weight to about 50 microgram/kg/body weight, from about 5 microgram/kg/body weight to about 40 microgram/kg/body weight, from about 5 microgram/kg/body weight to about 30 microgram/kg/body weight, from about 5 microgram/kg/body weight to about 20 microgram/kg/body weight, from about 5 microgram/kg/body weight to about 15 microgram/kg/body weight, from about 5 microgram/kg/body weight to about 10 microgram/kg/body weight, from about 10 microgram/kg/body weight to about 1000 microgram/kg/body weight, from about 10 microgram/kg/body weight to about 100 microgram/kg/body weight, from about 10 microgram/kg/body weight to about 75 microgram/kg/body weight, from about 10 microgram/kg/body weight to about 50 microgram/kg/body weight, from about 10 microgram/kg/body weight to about 40 microgram/kg/body weight, from about 10 microgram/kg/body weight to about 30 microgram/kg/body weight, from about 10 microgram/kg/body weight to about 20 microgram/kg/body weight, from about 10 microgram/kg/body weight to about 15 microgram/kg/body weight, from about 15 microgram/kg/body weight to about 1000 microgram/kg/body weight, from about 15 microgram/kg/body weight to about 100 microgram/kg/body weight, from about 15 microgram/kg/body weight to about 75 microgram/kg/body weight, from about 15 microgram/kg/body weight to about 50 microgram/kg/body weight, from about 15 microgram/kg/body weight to about 40 microgram/kg/body weight, from about 15 microgram/kg/body weight to about 30 microgram/kg/body weight, from about 15 microgram/kg/body weight to about 20 microgram/kg/body weight, from about 20 microgram/kg/body weight to about 1000 microgram/kg/body weight, from about 20 microgram/kg/body weight to about 100 microgram/kg/body weight, from about 20 microgram/kg/body weight to about 75 microgram/kg/body weight, from about 20 microgram/kg/body weight to about 50 microgram/kg/body weight, from about 20 microgram/kg/body weight to about 40 microgram/kg/body weight, from about 20 microgram/kg/body weight to about 30 microgram/kg/body weight, etc., can be administered, based on the numbers described above.

In certain embodiments, for example, but not limited to, administration of the superantigen conjugate, the effective amount or dose of the superantigen conjugate that is administered is an amount in the range of 0.01 to 500 µg/kg body weight of the subject, for example, 0.1-500 µg/kg body weight of the subject, and, for example, 1-100 µg/kg body weight of the subject.

It is envisioned that the effective amount or dose of the immunopotentiator that is administered in combination with the superantigen conjugate is a dose that results in an at least an additive but preferably a synergistic anti-tumor effect and does not interfere or inhibit the enhancement of the immune system or T-cell activation. If the immunopotentiator is administered simultaneously with the superantigen conjugate, then the immunopotentiator may be administered in a low dose such that it does not interfere with the mechanism of action of the superantigen conjugate.

Generally, a therapeutically effective amount of immunopotentiator, for example, the anti-PD-1 antibody, is in the range of 0.1 mg/kg to 100 mg/kg, e.g., 1 mg/kg to 100 mg/kg, 1 mg/kg to 10 mg/kg. For example, pembrolizumab (KEYTRUDA®) can be administered periodically at 2 mg/kg as an intravenous infusion. The amount of immunopotentiator administered will depend on variables such as the type and extent of disease or indication to be treated, the overall health of the patient, the in vivo potency of the superantigen conjugate and the immunopotentiator, the pharmaceutical formulation, and the route of administration.

V. Treatment Regimens and Indications

Treatment regimens may vary as well, and often depend on tumor type, tumor location, disease progression, and health and age of the patient. Certain types of tumor may require more aggressive treatment protocols, but at the same time, the patients may be unable to tolerate more aggressive treatment regimens. The clinician may often be best suited to make such decisions based on his or her skill in the art and the known efficacy and toxicity (if any) of the therapeutic formulations.

In a specific embodiment of the invention, the treatment methods of the invention comprise administration of a tumor-targeted superantigen in combination with an immunopotentiator to a patient in need thereof, i.e., a cancer patient. Such combination treatments include, for example, administration of any tumor-targeted superantigen and/or immunopotentiator as described herein. In a specific embodiment of the invention, the tumor-targeted super antigen comprises a bacterial superantigen including, but are not limited to, Staphylococcal enterotoxin (SE), *Streptococcus pyogenes* exotoxin (SPE), *Staphylococcus aureus* toxic shock-syndrome toxin (TSST-1), Streptococcal mitogenic exotoxin (SME), Streptococcal superantigen (SSA), Staphylococcal enterotoxin A (SEA), Staphylococcal enterotoxin B (SEB), and Staphylococcal enterotoxin E (SEE) conjugated to a targeting moiety.

In certain embodiments, the superantigen conjugate comprises a wild type or engineered superantigen sequence such as, the wild-type SEE sequence (SEQ ID NO: 1) or the wild type SEA sequence (SEQ ID NO: 2), either of which can be modified such that amino acids in any of the identified regions A-E (see, FIG. 2) are substituted with other amino acids. In certain embodiments, the superantigen incorporated in the conjugate is SEA/E-120 (SEQ ID NO: 3) or $SEA_{D227A}$ (SEQ ID NO: 4).

Specific examples of targeting moieties to be conjugated to the superantigens include, for example, any molecule that is able to bind to a cellular molecule and preferably a disease specific molecule such as a cancer cell specific molecule. The targeting moiety can be selected from antibodies, including antigen binding fragments, soluble T-cell receptors, growth factors, interleukins, hormones, etc. Exemplary cancer targeting antibodies can include, but are not limited to, anti-CD19, anti-CD20 antibodies, anti-5T4 antibodies, anti-Ep-CAM antibodies, anti-Her-2/neu antibodies, anti-EGFR antibodies, anti-CEA antibodies, anti-prostate specific membrane antigen (PSMA) antibodies, and anti-IGF-1R antibodies. In one embodiment, the superantigen can be conjugated to an immunologically reactive antibody fragment such as C215Fab, 5T4Fab (see, WO8907947) or C242Fab (see, WO9301303).

Examples of such tumor-targeted superantigens include C215Fab-SEA (SEQ ID NO: 5), 5T4Fab-$SEA_{D227A}$ (SEQ ID NO: 6) and 5T4Fab-SEA/E-120 (SEQ ID NO: 7). In a preferred embodiment, the superantigen conjugate is 5T4 Fab-SEA/E-120 known in the art as Naptumomab estafenatox/ANYARA®, which comprises two polypeptide sequences that together define an Fab fragment of an anti-5T4 antibody, where one of the polypeptide sequences further comprises the SEA/E-120 superantigen namely SEQ ID. NO: 8 (chimeric $V_H$ chain of 5T4 Fab coupled by three amino acid linker to SEA/E-120) and SEQ ID. NO: 9 (chimeric $V_L$ chain of 5T4 Fab).

In a preferred embodiment, the compositions of the invention comprise the tumor-targeted superantigen 5T4Fab-SEA/E-120, known in the art as naptumomab estafenatox/ANYARA® in combination with a PD-1 inhibitor, such as an anti-PD-1 antibody, for example, nivolumab (Bristol-Myers Squibb Co.), pembrolizumab (KEYTRUDA®, Merck & Co.), MK-3475 (Merck & Co), pidilizumab (CureTech), AMP-224 (AstraZeneca/Medimmune) and AMP-514 (AstraZeneca/Medimmune) or an anti-PD-L1 antibody such as MPDL3280A (Genentech/Roche), MEDI-4736 (AstraZeneca/Medimmune) and MSB0010718C (EMD Serono/Merck KGA).

In a specific embodiment of the invention, the compositions comprise the targeted superantigen naptumomab estafenatox (ANYARA®) in combination with one or more anti-PD-1 antibodies including nivolumab (Bristol-Myers Squibb Co.), pembrolizumab (KEYTRUDA®, Merck & Co.), Atezolizumab (formerly MPDL3280A), MEDI4736, Avelumab, and PDR001.

Furthermore, the superantigen conjugate and immunopotentiator may be co-administered together or sequentially with one or more additional agents that enhance the potency and/or selectively of the therapeutic effect. Such agents include, for example, corticosteroids, additional immune modulators, and those compounds designed to reduce the patient's possible immunoreactivity to the administered superantigen conjugate. For example, immunoreactivity to the administered superantigen may be reduced via co-administration with, for example, an anti-CD20 antibody and/or an anti-CD19 antibody, that reduces the production of anti-superantigen antibodies in the subject.

Preferably, patients to be treated will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

In certain embodiments, the treatment regimen of the present invention may involve contacting the neoplasm or tumor cells with the superantigen conjugate and the immunopotentiator at the same time. This may be achieved by contacting the cell with a single composition or pharmacological formulation that includes both agents, or by contacting the cell with two distinct compositions or formulations, at the same time, wherein one composition includes the superantigen conjugate and the other includes the immunopotentiator.

Alternatively, the superantigen conjugate may precede or follow the immunopotentiator by intervals ranging from minutes, days to weeks. In embodiments where the other immunopotentiator and the superantigen conjugate are applied separately to the cell, one should ensure that a significant period of time does not expire between the time of each delivery, such that the superantigen conjugate and immunopotentiator would still be able to exert an advantageously combined effect on the cell. In such instances, it is contemplated that one may contact the cell with both modalities within about 12-72 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the superantigen conjugate being "A" and the immunopotentiator being "B": AB/A, B/A/B, BB/A, A/A/B, A/B/B, B/A/A, A/BBB, B/A/B/B, BBB/A, B/B/A/B, A/A/B/B, AB/AB, A/B/B/A, B/B/A/A, B/A/B/A, B/A/A/B, A/A/A/B, B/A/A/A, A/B/A/A, and A/A/B/A.

It is further envisioned that the present invention can be used in combination with surgical intervention. In the case of surgical intervention, the present invention may be used preoperatively, e.g., to render an inoperable tumor subject to resection. Alternatively, the present invention may be used at the time of surgery, and/or thereafter, to treat residual or metastatic disease. For example, a resected tumor bed may be injected or perfused with a formulation comprising the tumor-targeted superantigen and/or the immunopotentiator. The perfusion may be continued post-resection, for example, by leaving a catheter implanted at the site of the surgery. Periodic post-surgical treatment also is envisioned. Any combination of the invention therapy with surgery is within the scope of the invention.

Continuous administration also may be applied where appropriate, for example, where a tumor is excised and the tumor bed is treated to eliminate residual, microscopic disease. Delivery via syringe or cauterization is preferred. Such continuous perfusion may take place for a period from about 1-2 hours, to about 2-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

A typical course of treatment, for a primary tumor or a post-excision tumor bed, may involve multiple doses. Typical primary tumor treatment may involve a 6 dose application over a two-week period. The two-week regimen may be repeated one, two, three, four, five, six or more times. During a course of treatment, the need to complete the planned dosings may be re-evaluated.

Immunotherapy with the superantigen conjugate often results in rapid (within hours) and powerful polyclonal activation of T lymphocytes. A superantigen conjugate treatment cycle may include 4 to 5 daily intravenous superantigen conjugate drug injections. Such treatment cycles can be given in e.g., 4 to 6 week intervals. The inflammation with infiltration of CTLs into the tumor is one of the major effectors of the anti-tumor therapeutic superantigens. After a short period of massive activation and differentiation of CTLs, the T-cell response declines rapidly (within 4-5 days) back to base line levels. Thus, the period of lymphocyte proliferation, during which cytostatic drugs may interfere with superantigen treatment is short and well-defined. Only with the superantigen/immunopotentiator therapy of the instant invention is such a distinct time frame for activity plausible, thereby allowing the novel integrated high dose cytostatic agent/immunotherapy treatment.

It is contemplated that a number of cancers may be treated using the methods and compositions described herein, including but not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemia, uterine cancer, breast cancer, prostate cancer, ovarian cancer, pancreatic cancer, colon cancer, multiple myeloma, neuroblastoma, NPC, bladder cancer, cervical cancer and the like.

Moreover, the cancer that may be treated using the methods and compositions described herein may be based upon the body location and/or system to be treated, for example, but not limited to bone (e.g., Ewing's Family of tumors, osteosarcoma); brain (e.g., adult brain tumor, (e.g., adult brain tumor, brain stem glioma (childhood), cerebellar astrocytoma (childhood), cerebral astrocytoma/malignant glioma (childhood), ependymoma (childhood). medulloblastoma (childhood), supratentorial primitive neuroectodermal tumors and pineoblastoma (childhood), visual pathway and hypothalamic glioma (childhood) and childhood brain tumor (other)); breast (e.g., female or male breast cancer); digestive/gastrointestinal (e.g., anal cancer, bile duct cancer (extrahepatic), carcinoid tumor (gastrointestinal), colon cancer, esophageal cancer, gallbladder cancer, liver cancer (adult primary), liver cancer (childhood), pancreatic cancer, small intestine cancer, stomach (gastric) cancer); endocrine (e.g., adrenocortical carcinoma, carcinoid tumor (gastrointestinal), islet cell carcinoma (endocrine pancreas), parathyroid cancer, pheochromocytoma, pituitary tumor, thyroid cancer); eye (e.g., melanoma (intraocular), retinoblastoma); genitourinary (e.g., bladder cancer, kidney (renal cell) cancer, penile cancer, prostate cancer, renal pelvis and ureter cancer (transitional cell), testicular cancer, urethral cancer, Wilms' Tumor and other childhood kidney tumors); germ cell (e.g., extracranial germ cell tumor (childhood), extragonadal germ cell tumor, ovarian germ cell tumor, testicular cancer); gynecologic (e.g., cervical cancer, endometrial cancer, gestational trophoblastic tumor, ovarian epithelial cancer, ovarian germ cell tumor, ovarian low malignant potential tumor, uterine sarcoma, vaginal cancer, vulvar cancer); head and neck (e.g., hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, parathyroid cancer, salivary gland cancer); lung (e.g., non-small cell lung cancer, small cell lung cancer); lymphoma (e.g., AIDS-Related Lymphoma, cutaneous T-cell lymphoma, Hodgkin's Lymphoma (adult), Hodgkin's Lymphoma (childhood), Hodgkin's Lymphoma during pregnancy, mycosis fungoides, Non-Hodgkin's Lymphoma (adult), Non-Hodgkin's Lymphoma (childhood), Non-Hodgkin's Lymphoma during pregnancy, primary central nervous system lymphoma, Sezary Syndrome, T-cell lymphoma (cutaneous), Waldenstrom's Macroglobulinemia); musculoskeletal (e.g., Ewing's Family of tumors, osteosarcoma/malignant fibrous histiocytoma of bone, rhabdomyosarcoma (childhood), soft tissue sarcoma (adult), soft tissue sarcoma (childhood), uterine sarcoma); neurologic (e.g., adult brain tumor, childhood brain tumor (e.g., brain stem glioma, cerebellar astrocytoma, cerebral astrocytoma/ malignant glioma, ependymoma, medulloblastoma, supratentorial primitive neuroectodermal tumors and pineoblastoma, visual pathway and hypothalamic glioma, other brain tumors), neuroblastoma, pituitary tumor primary central nervous system lymphoma); respiratory/thoracic (e.g., non-small cell lung cancer, small cell lung cancer, malignant mesothelioma, thymoma and thymic carcinoma); and skin (e.g., cutaneous T-cell lymphoma, Kaposi's sarcoma, melanoma, and skin cancer).

It is understood that the method can be used to treat a variety of cancers, for example, a cancer selected from the group consisting of breast cancer, cervical cancer, colorectal cancer, gastric cancer, non-small cell lung cancer, ovarian cancer, pancreatic cancer, prostate cancer, renal cell cancer, and skin cancer.

Yet further, the cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a renal cancer cell, an ovarian cancer cell, a lymphatic cancer cell, a skin cancer cell, a brain cancer cell, a bone cancer cell, or a soft tissue cancer cell. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

VI. Kits

In addition, the invention provides kits comprising, for example, a first container containing a superantigen conjugate and a second container containing an immunopotentiator such as an anti-PD-1 antibody. Such a kit may also contain additional agents such as, for example, corticosteroid or another lipid modulator. The container means may itself be a syringe, pipette, and/or other such like apparatus, from which the formulation may be applied to a specific area of the body, injected into an animal, and/or applied and/or mixed with the other components of the kit.

The kits may comprise a suitably aliquoted superantigen conjugate and/or immunopotentiator, and optionally, lipid and/or additional agent compositions of the present invention. The components of the kits may be packaged either in aqueous media or in lyophilized form. When the components of the kit are provided in one and/or more liquid solutions, the liquid solution is a sterile aqueous solution.

Practice of the invention will be more fully understood from the foregoing examples, which are presented herein for illustrative purposes only, and should not be construed as limiting the invention in any way.

EXAMPLES

Example 1

Combination Therapy Of Naptumomab Estafenatox/ANYARA® And An Anti-PD-1 Inhibitor Against The NSCLC Tumor Cell Line This example describes an in-vitro study testing the anti-cancer effect of the combination of a tumor targeted superantigen, naptumomab estafenatox/ANYARA®, and an anti-PD-1 antibody, pembrolizumab/KEYTRUDA®, against the HCC827 non-small-cell lung (NSCLC) tumor cell line.

Peripheral blood mononuclear cells (PBMCs) from healthy donors were incubated for 4 days with 10 ng/ml of Staphylococcal enterotoxin A (SEA). T-cells were then isolated and incubated with IL-2 for 1 additional day. $1\times10^4$ HCC827 cells per well were incubated in 96-well plates for 1 hour with T-cells and pembrolizumab/KEYTRUDA® at a concentration of 0.2 µg/ml. Effector:Target ratio (T-cells: HCC827 cells) was 8:1. After 1 hour of incubation with or without pembrolizumab/KEYTRUDA®, naptumomab estafenatox/ANYARA® in different concentrations (0, 0.1 µg/ml, and 10 µg/ml) was added to the wells and the plates were incubated for an additional 48 hours. At the end of the treatment the culture supernatant was removed, including suspended T-cells and tumors cells, and the attached tumor cells were washed one time with culture medium. The viability of residual HCC827 was tested with a CCK8 kit (Cell Counting Kit-8, Sigma Aldrich) according to the manufacturer's protocol. The viability of control group was normalized to 100%. Viability of the cancer cells (%)=(OD value of treatment group/OD value of control group)×100.

Figure 4:
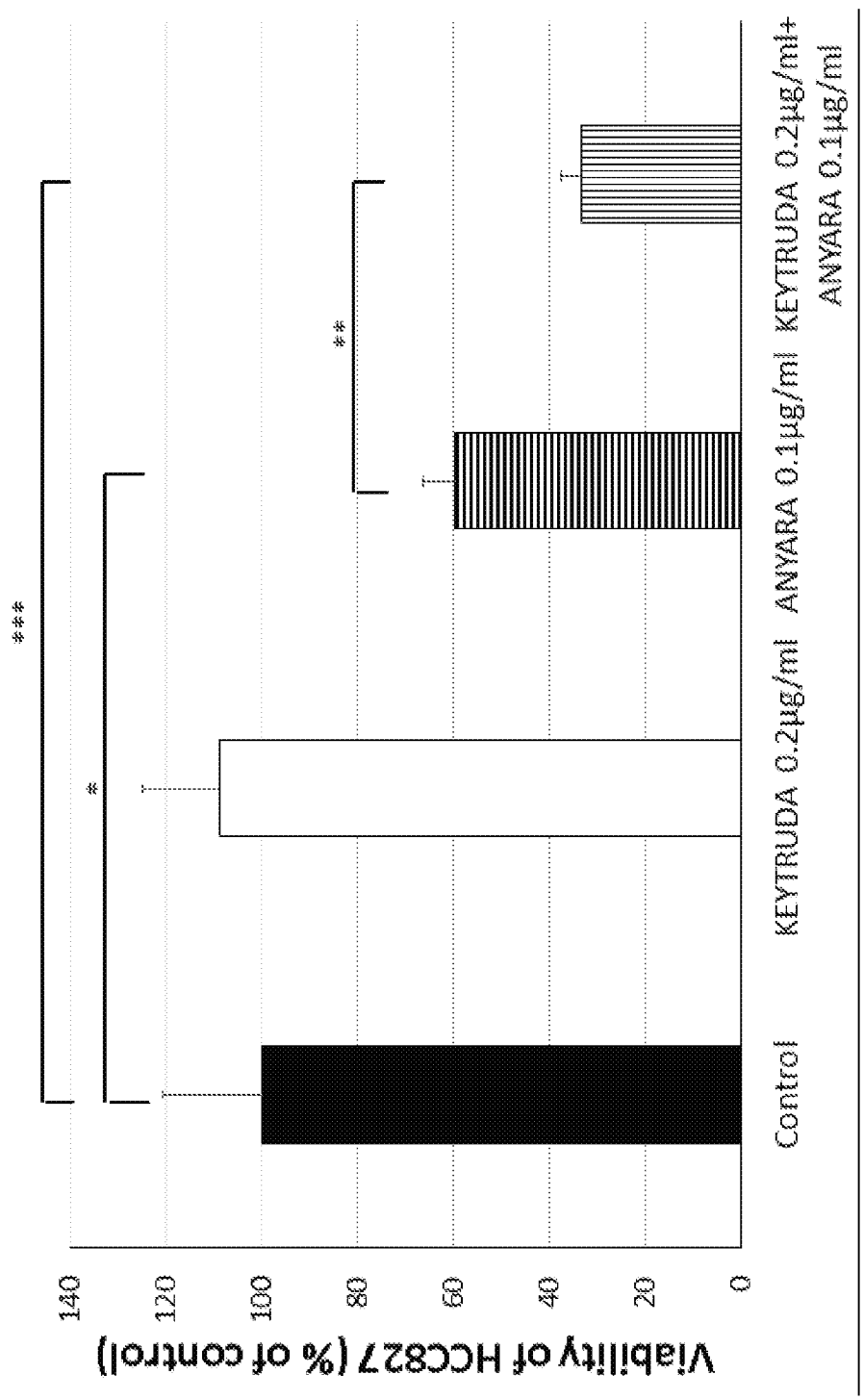
FIG. 4 is a bar chart illustrating the effect of naptumomab estafenatox/ANYARA® and pembrolizumab/ KEYTRUDA® alone or in combination on the viability of the non-small-cell lung (NSCLC) cell line, HCC827. The survival rates of HCC827 cells co-cultured with T-cells were measured after 48 hours of treatment with naptumomab estafenatox/ANYARA® (0.1 µg/ml) and/or pembrolizumab/ KEYTRUDA® (0.2 µg/ml) or medium alone (Control). n=3-6; mean±SD *$p<0.05$, $p<0.02$; *$p<0.005$, as determined by two-tailed Student's t test.
Figure 5:
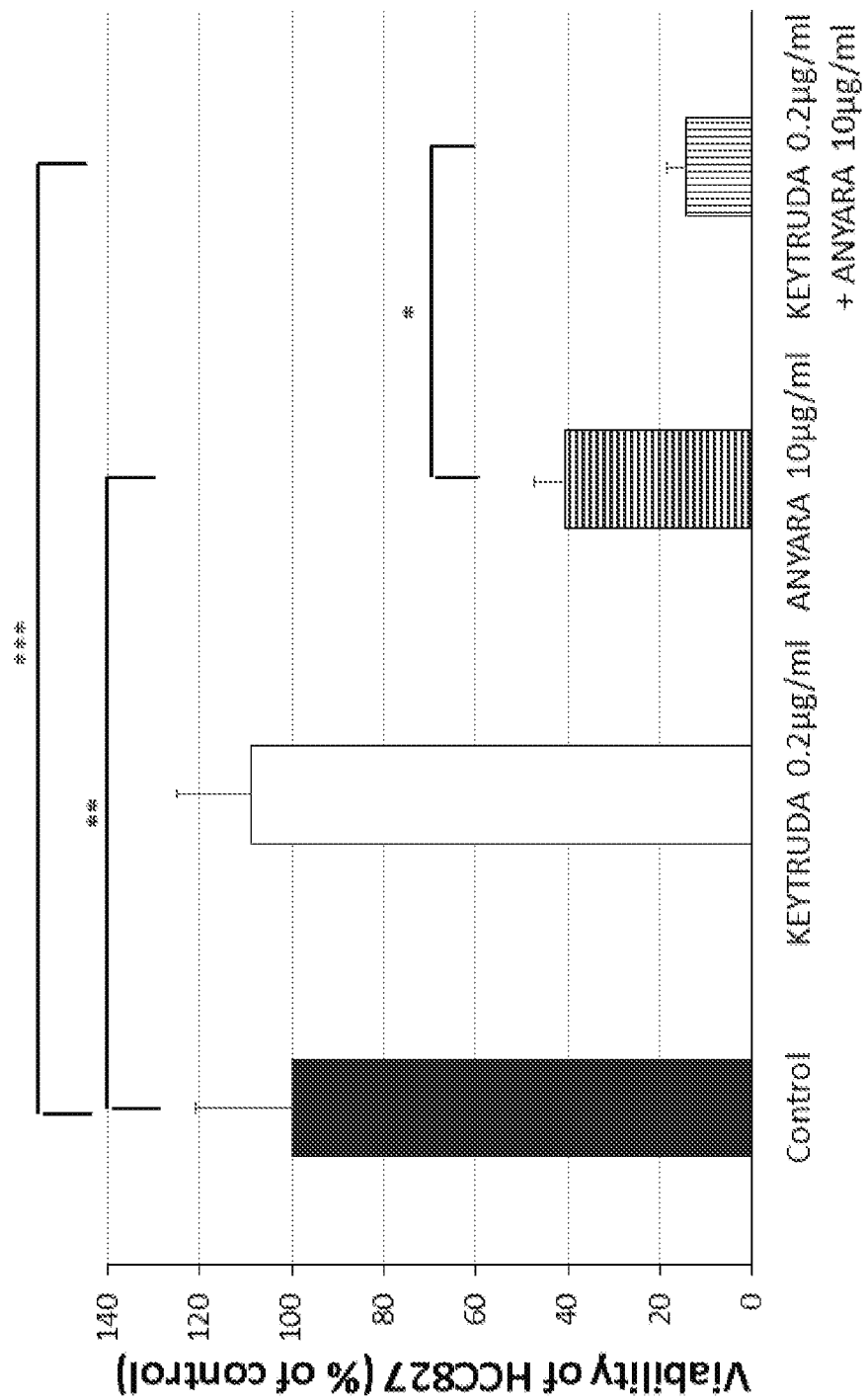
FIG. 5 is a bar chart illustrating the effect of naptumomab estafenatox/ANYARA® and pembrolizumab/ KEYTRUDA® alone or in combination on the viability of the NSCLC cell line, HCC827. The survival rates of HCC827 cells co-cultured with T-cells were measured after 48 hours of treatment with naptumomab estafenatox/ANYARA® (10 µg/ml) and/or pembrolizumab/KEYTRUDA® (0.2 µg/ml) or medium alone (Control). n=3-6; mean±SD. *$p=0.005$, $p<0.005$; *$p<0.0005$, as determined by two-tailed Student's t test.

As shown in FIG. 4 and FIG. 5, the combination of naptumomab estafenatox/ANYARA® with pembrolizumab/KEYTRUDA® had the strongest effect on HCC827 cell viability. Although naptumomab estafenatox/ANYARA® alone at both concentrations decreased the viability of HCC827 cells, it was much less effective in comparison to the combination of naptumomab estafenatox/ANYARA® with pembrolizumab/KEYTRUDA®. Pembrolizumab/KEYTRUDA® at the tested concentration of 0.2 µg/ml had no effect on the viability of the cancer cells. Naptumomab estafenatox/ANYARA® at the lower concentration of 0.1 µg/ml decreased the viability of HCC827 cells to 60±9.4% (p<0.05 vs. control) whereas the combination of naptumomab estafenatox/ANYARA® with pembrolizumab/KEYTRUDA® reduced the viability of the cells to 33±4.9% (p<0.005 vs. control; p<0.05 vs. naptumomab estafenatox/ANYARA®) (FIG. 4). Naptumomab estafenatox/ANYARA® at the higher concentration (10 µg/ml) had a stronger effect than at the lower concentration, reducing the viability of the cancer cells to 40±6.6% (p<0.005 vs. control), however, also at this concentration the combination of naptumomab estafenatox/ANYARA® with pembrolizumab/KEYTRUDA° was significantly more effective and reduced the viability of the cells to 14±4.2% (p<0.0005 vs. control; p=0.005 vs. naptumomab estafenatox/ANYARA®) (FIG. 5).

Taken together, these results demonstrate the synergistic effect of immunopotentiator anti-PD-1 (pembrolizumab/KEYTRUDA®) with tumor targeted superantigen (naptumomab estafenatox/ANYARA®) and support the concept that administration of a cancer targeted superantigen, together with an immunopotentiator, can result in an enhanced anti-cancer effect that is greater than the additive effect of each agent when administered alone.

Example 2

Combination Therapy Of Tumor Targeted Superantigen And A Murine Anti-PD-1 Inhibitor In A B16 Melanoma Mouse Model This example describes a study testing the effect of a tumor targeted superantigen, C215Fab-SEA, and a murine anti-PD-1 antibody against the murine B16-EpCAM melanoma model in vivo. The combination therapy of tumor targeted superantigen and anti-PD-1 was tested in a syngeneic tumor model using low immunogenic B16 melanoma transfected with the human colon carcinoma antigen EpCAM, which is recognized by the C215 antibody. The tumor targeted superantigen C215Fab-SEA is a fusion protein which includes a tumor-reactive mAb (C215Fab) and the bacterial superantigen staphylococcal enterotoxin A (SEA). C215Fab-SEA was used instead of naptumomab estafenatox/ANYARA® to facilitate in vivo murine experiments.

For the study, C57Bl/6 mice were inoculated intravenously (IV) with $1.75\times10^5$ of B16-EpCAM melanoma cells into the tail vein to induce lung tumors. Mice were treated on days 5 to 8 with daily IV injections of C215Fab-SEA (0.5 µg/mouse) and/or intraperitoneal (IP) injections of anti-PD-1 mAb (200 µg/mouse) twice a week. The control group was treated with PBS at the same mode of administration and regiment as the combination therapy group. On day 21 the mice were killed and the lungs were removed. After fixation in Bouin's solution for at least 24 hours, the number of lung tumors were counted.

Figure 6:
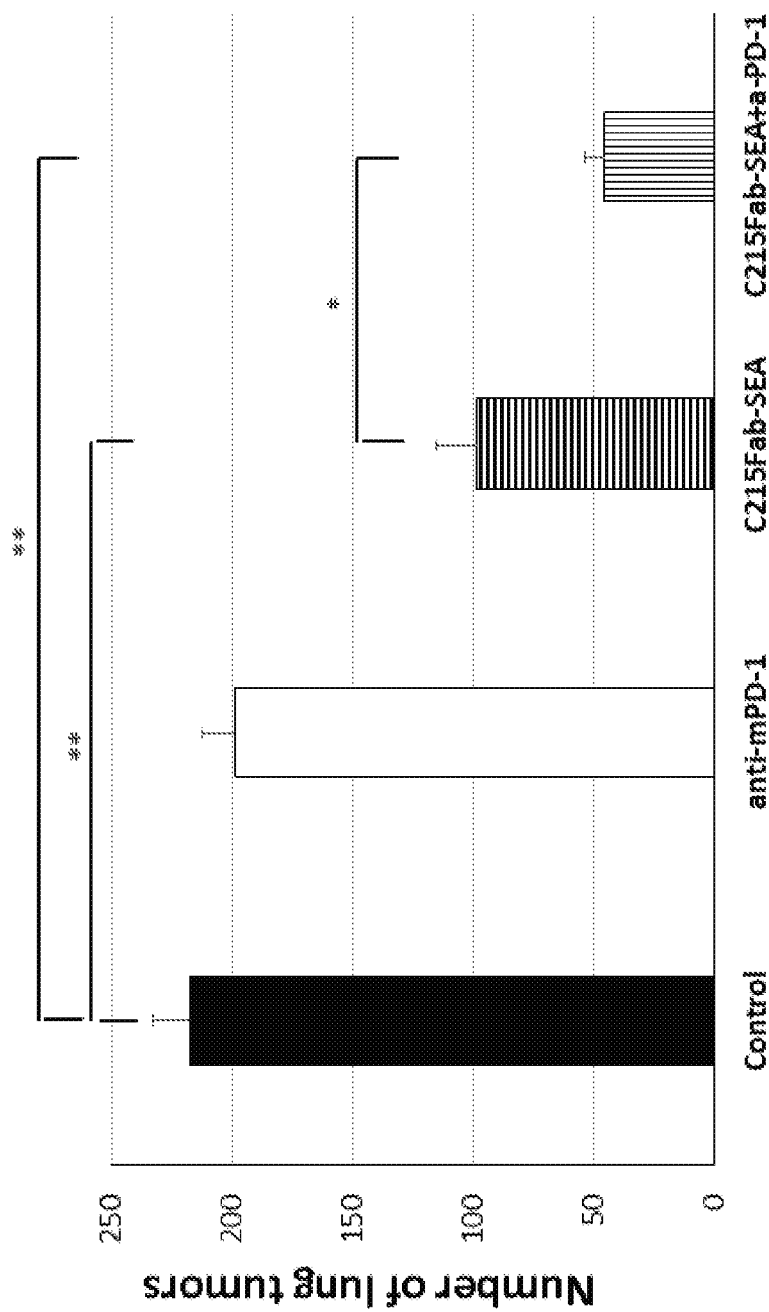
FIG. 6 is a bar chart illustrating the effect of C215Fab-SEA and anti-PD-1 mAb alone or in combination on lung tumor burden in the B16-EpCAM mice melanoma model. Mice were inoculated with B16-EpCAM melanoma cells intravenously and were treated with C215Fab-SEA (0.5 µg/mouse) and/or anti-PD-1 mAb (200 µg/mouse). Control group was injected with PBS. On day 21, mice were sacrificed, lungs were removed and the number of tumors was counted. n=7-8 mice/group; mean±SEM. *$p=0.05$, **$p<0.001$, as determined by ANOVA.

The results of the study are presented in FIG. 6. As was expected, because B16 melanoma is a low immunogenic tumor, anti-PD-1 mAb monotherapy had no effect on the number of lung tumors. C215Fab-SEA alone reduced the number of B16 lung tumors by approximately 50%, from 217.1±15.9 (mean±SEM) tumors in the control treated mice to 98.8±16.4 at day 21. C215Fab-SEA and the anti-PD-1 mAb in combination reduced the number of tumors by approximately 80%, a significant reduction (p<0.05) compared to the monotherapy.

These results further demonstrate the potential of combining tumor targeted superantigen together with an immunopotentiator for the treatment of low immunogenic tumors.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating a cancer in a subject in need thereof, the method comprising administering to the subject (i) an effective amount of a superantigen conjugate comprising a first protein chain comprising SEQ ID NO: 8 and a second protein chain comprising SEQ ID NO: 9 that together bind a 5T4 cancer antigen expressed by cancerous cells within the subject and (ii) an effective amount of an anti-PD-1 antibody selected from nivolumab and pembrolizumab, thereby to treat the cancer, wherein the cancer is selected from colon cancer and breast cancer.

2. The method of claim 1, wherein the cancer is colon cancer.

3. The method of claim 2, wherein the anti-PD-1 antibody is nivolumab.

4. The method of claim 2, wherein the anti-PD-1 antibody is pembrolizumab.

5. The method of claim 2, wherein the superantigen conjugate is administered to the subject before the anti-PD-1 antibody.

6. The method of claim 2, wherein the superantigen conjugate is administered to the subject at the same time as the anti-PD-1 antibody.

7. The method of claim 2, wherein the superantigen conjugate is administered to the subject after the anti-PD-1 antibody.

8. The method of claim 1, wherein the cancer is breast cancer.

9. The method of claim 8, wherein the anti-PD-1 antibody is nivolumab.

10. The method of claim 8, wherein the anti-PD-1 antibody is pembrolizumab.

11. The method of claim 8, wherein the superantigen conjugate is administered to the subject before the anti-PD-1 antibody.

12. The method of claim 8, wherein the superantigen conjugate is administered to the subject at the same time as the anti-PD-1 antibody.

13. The method of claim 8, wherein the superantigen conjugate is administered to the subject after the anti-PD-1 antibody.

* * * * *

SEQUENCE LISTING

```
<160> NUMBER OF SEQ ID NOS: 10

<210> SEQ ID NO 1
<211> LENGTH: 233
<212> TYPE: PRT
<213> ORGANISM: Staphylococcus sp

<400> SEQUENCE: 1

Ser Glu Lys Ser Glu Glu Ile Asn Glu Lys Asp Leu Arg Lys Lys Ser
1               5                   10                  15

Glu Leu Gln Arg Asn Ala Leu Ser Asn Leu Arg Gln Ile Tyr Tyr Tyr
                20                  25                  30

Asn Glu Lys Ala Ile Thr Glu Asn Lys Glu Ser Asp Asp Gln Phe Leu
            35                  40                  45

Glu Asn Thr Leu Leu Phe Lys Gly Phe Phe Thr Gly His Pro Trp Tyr
        50                  55                  60

Asn Asp Leu Leu Val Asp Leu Gly Ser Lys Asp Ala Thr Asn Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Ile Asp Gly Lys Gln Thr Thr Val Pro Ile Asp Lys Val Lys
    130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
            180                 185                 190

Thr Val Ser Tyr Asp Leu Phe Asp Ala Gln Gly Gln Tyr Pro Asp Thr
        195                 200                 205

Leu Leu Arg Ile Tyr Arg Asp Asn Lys Thr Ile Asn Ser Glu Asn Leu
    210                 215                 220

His Ile Asp Leu Tyr Leu Tyr Thr Thr
225                 230

<210> SEQ ID NO 2
<211> LENGTH: 233
<212> TYPE: PRT
<213> ORGANISM: Staphylococcus sp

<400> SEQUENCE: 2
```

```
Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Glu Lys Ala Lys Thr Glu Asn Lys Glu Ser His Asp Gln Phe Leu
            35                  40                  45

Gln His Thr Ile Leu Phe Lys Gly Phe Phe Thr Asp His Ser Trp Tyr
        50                  55                  60

Asn Asp Leu Leu Val Asp Phe Asp Ser Lys Asp Ile Val Asp Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Leu Asp Gly Lys Gln Asn Thr Val Pro Leu Glu Thr Val Lys
    130                 135                 140

Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                165                 170                 175

Gly Lys Val Gln Arg Gly Leu Ile Val Phe His Thr Ser Thr Glu Pro
            180                 185                 190

Ser Val Asn Tyr Asp Leu Phe Gly Ala Gln Gly Gln Tyr Ser Asn Thr
        195                 200                 205

Leu Leu Arg Ile Tyr Arg Asp Asn Lys Thr Ile Asn Ser Glu Asn Met
    210                 215                 220

His Ile Asp Ile Tyr Leu Tyr Thr Ser
225                 230

<210> SEQ ID NO 3
<211> LENGTH: 233
<212> TYPE: PRT
<213> ORGANISM: Artificial Sequence
<220> FEATURE:
<223> OTHER INFORMATION: Mutated Protein

<400> SEQUENCE: 3

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Ser Lys Ala Ile Thr Ser Ser Glu Lys Ser Ala Asp Gln Phe Leu
            35                  40                  45

Thr Asn Thr Leu Leu Phe Lys Gly Phe Phe Thr Gly His Pro Trp Tyr
        50                  55                  60

Asn Asp Leu Leu Val Asp Leu Gly Ser Thr Ala Ala Thr Ser Glu Tyr
65                  70                  75                  80

Glu Gly Ser Ser Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125
```

```
Leu Trp Ile Asp Gly Lys Gln Thr Thr Val Pro Ile Asp Lys Val Lys
        130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
                180                 185                 190

Thr Val Ser Tyr Asp Leu Phe Asp Ala Gln Gly Gln Tyr Pro Asp Thr
            195                 200                 205

Leu Leu Arg Ile Tyr Arg Asp Asn Thr Thr Ile Ser Ser Thr Ser Leu
        210                 215                 220

Ser Ile Ser Leu Tyr Leu Tyr Thr Thr
225                 230

<210> SEQ ID NO 4
<211> LENGTH: 233
<212> TYPE: PRT
<213> ORGANISM: Artificial Sequence
<220> FEATURE:
<223> OTHER INFORMATION: Mutated Protein

<400> SEQUENCE: 4

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
                20                  25                  30

Asn Glu Lys Ala Lys Thr Glu Asn Lys Glu Ser His Asp Gln Phe Leu
            35                  40                  45

Gln His Thr Ile Leu Phe Lys Gly Phe Phe Thr Asp His Ser Trp Tyr
        50                  55                  60

Asn Asp Leu Leu Val Asp Phe Asp Ser Lys Asp Ile Val Asp Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
                100                 105                 110

Leu His Asp Asn Asn Arg Leu Thr Glu Glu Lys Lys Val Pro Ile Asn
        115                 120                 125

Leu Trp Leu Asp Gly Lys Gln Asn Thr Val Pro Leu Glu Thr Val Lys
        130                 135                 140

Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                165                 170                 175

Gly Lys Val Gln Arg Gly Leu Ile Val Phe His Thr Ser Thr Glu Pro
                180                 185                 190

Ser Val Asn Tyr Asp Leu Phe Gly Ala Gln Gly Gln Tyr Ser Asn Thr
            195                 200                 205

Leu Leu Arg Ile Tyr Arg Asp Asn Lys Thr Ile Asn Ser Glu Asn Met
        210                 215                 220

His Ile Ala Ile Tyr Leu Tyr Thr Ser
225                 230

<210> SEQ ID NO 5
```

<211> LENGTH: 679
<212> TYPE: PRT
<213> ORGANISM: Artificial Sequence
<220> FEATURE:
<223> OTHER INFORMATION: Conjugated Protein
<220> FEATURE:
<221> NAME/KEY: MISC_FEATURE
<222> LOCATION: (460)..(679)
<223> OTHER INFORMATION: Light Chain

<400> SEQUENCE: 5

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Tyr Ile Tyr Thr Asn Tyr Asn Gln Glu Phe
    50                  55                  60

Lys Asp Lys Val Thr Leu Thr Val Asp Glu Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Pro Tyr Gly Tyr Asp Glu Tyr Gly Leu Asp Tyr Trp Gly
            100                 105                 110

Gln Gly Thr Ser Val Thr Val Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Ser Gly
    210                 215                 220

Gly Pro Ser Glu Lys Ser Glu Glu Ile Asn Glu Lys Asp Leu Arg Lys
225                 230                 235                 240

Lys Ser Glu Leu Gln Gly Thr Ala Leu Gly Asn Leu Lys Gln Ile Tyr
                245                 250                 255

Tyr Tyr Asn Glu Lys Ala Lys Thr Glu Asn Lys Glu Ser His Asp Gln
            260                 265                 270

Phe Leu Gln His Thr Ile Leu Phe Lys Gly Phe Phe Thr Asp His Ser
        275                 280                 285

Trp Tyr Asn Asp Leu Leu Val Asp Phe Asp Ser Lys Asp Ile Val Asp
    290                 295                 300

Lys Tyr Lys Gly Lys Lys Val Asp Leu Tyr Gly Ala Tyr Tyr Gly Tyr
305                 310                 315                 320

Gln Cys Ala Gly Gly Thr Pro Asn Lys Thr Ala Cys Met Tyr Gly Gly
                325                 330                 335

Val Thr Leu His Asp Asn Asn Arg Leu Thr Glu Glu Lys Lys Val Pro
            340                 345                 350

Ile Asn Leu Trp Leu Asp Gly Lys Gln Asn Thr Val Pro Leu Glu Thr
```

```
                355                 360                 365
Val Lys Thr Asn Lys Asn Val Thr Val Gln Glu Leu Asp Leu Gln
370                 375                 380

Ala Arg Arg Tyr Leu Gln Glu Lys Tyr Asn Leu Tyr Asn Ser Asp Val
385                 390                 395                 400

Phe Asp Gly Lys Val Gln Arg Gly Leu Ile Val Phe His Thr Ser Thr
                    405                 410                 415

Glu Pro Ser Val Asn Tyr Asp Leu Phe Gly Ala Gln Gly Gln Tyr Ser
                420                 425                 430

Asn Thr Leu Leu Arg Ile Tyr Arg Asp Asn Lys Thr Ile Asn Ser Glu
            435                 440                 445

Asn Met His Ile Asp Ile Tyr Leu Tyr Thr Ser Asp Ile Val Met Thr
        450                 455                 460

Gln Ser Pro Ser Ser Leu Thr Val Thr Ala Gly Glu Lys Val Thr Met
465                 470                 475                 480

Asn Cys Lys Ser Ser Gln Ser Leu Leu Asn Ser Arg Asn Gln Lys Asn
                    485                 490                 495

Tyr Leu Thr Trp Tyr Gln Gln Lys Pro Gly Gln Pro Pro Lys Leu Leu
                500                 505                 510

Ile Tyr Trp Ala Ser Thr Arg Glu Ser Gly Val Pro Asp Arg Phe Thr
            515                 520                 525

Gly Ser Gly Ser Gly Thr Asp Phe Thr Leu Thr Ile Ser Ser Val Gln
        530                 535                 540

Ala Glu Asp Leu Ala Val Tyr Tyr Cys Gln Asn Asp Tyr Val Tyr Pro
545                 550                 555                 560

Leu Thr Phe Gly Ala Gly Thr Lys Leu Glu Leu Lys Arg Ala Asp Ala
                    565                 570                 575

Ala Pro Thr Val Ser Ile Phe Pro Pro Ser Ser Glu Gln Leu Thr Ser
                580                 585                 590

Gly Gly Ala Ser Val Val Cys Phe Leu Asn Asn Phe Tyr Pro Lys Asp
            595                 600                 605

Ile Asn Val Lys Trp Lys Ile Asp Gly Ser Glu Arg Gln Asn Gly Val
        610                 615                 620

Leu Asn Ser Trp Thr Asp Gln Asp Ser Lys Asp Ser Thr Tyr Ser Met
625                 630                 635                 640

Ser Ser Thr Leu Thr Leu Thr Lys Asp Glu Tyr Glu Arg His Asn Ser
                    645                 650                 655

Tyr Thr Cys Glu Ala Thr His Lys Thr Ser Thr Ser Pro Ile Val Lys
                660                 665                 670

Ser Phe Asn Arg Asn Glu Ser
            675

<210> SEQ ID NO 6
<211> LENGTH: 672
<212> TYPE: PRT
<213> ORGANISM: Artificial Sequence
<220> FEATURE:
<223> OTHER INFORMATION: Mutated and Conjugated Protein
<220> FEATURE:
<221> NAME/KEY: MISC_FEATURE
<222> LOCATION: (459)..(672)
<223> OTHER INFORMATION: Light Chain

<400> SEQUENCE: 6

Glu Val Gln Leu Gln Gln Ser Gly Pro Asp Leu Val Lys Pro Gly Ala
1               5                   10                  15
```

-continued

```
Ser Val Lys Ile Ser Cys Lys Ala Ser Gly Tyr Ser Phe Thr Gly Tyr
             20                  25                  30

Tyr Met His Trp Val Lys Gln Ser His Gly Lys Ser Leu Glu Trp Ile
             35                  40                  45

Gly Arg Ile Asn Pro Asn Asn Gly Val Thr Leu Tyr Asn Gln Lys Phe
 50                  55                  60

Lys Asp Lys Ala Ile Leu Thr Val Asp Lys Ser Ser Thr Thr Ala Tyr
 65                  70                  75                  80

Met Glu Leu Arg Ser Leu Thr Ser Glu Asp Ser Ala Val Tyr Tyr Cys
             85                  90                  95

Ala Arg Ser Thr Met Ile Thr Asn Tyr Val Met Asp Tyr Trp Gly Gln
            100                 105                 110

Val Thr Ser Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Ser Gly Gly
210                 215                 220

Pro Ser Glu Lys Ser Glu Glu Ile Asn Glu Lys Asp Leu Arg Lys Lys
225                 230                 235                 240

Ser Glu Leu Gln Gly Thr Ala Leu Gly Asn Leu Lys Gln Ile Tyr Tyr
            245                 250                 255

Tyr Asn Glu Lys Ala Lys Thr Glu Asn Lys Glu Ser His Asp Gln Phe
            260                 265                 270

Leu Gln His Thr Ile Leu Phe Lys Gly Phe Phe Thr Asp His Ser Trp
            275                 280                 285

Tyr Asn Asp Leu Leu Val Asp Phe Asp Ser Lys Asp Ile Val Asp Lys
            290                 295                 300

Tyr Lys Gly Lys Lys Val Asp Leu Tyr Gly Ala Tyr Tyr Gly Tyr Gln
305                 310                 315                 320

Cys Ala Gly Gly Thr Pro Asn Lys Thr Ala Cys Met Tyr Gly Gly Val
            325                 330                 335

Thr Leu His Asp Asn Asn Arg Leu Thr Glu Glu Lys Lys Val Pro Ile
            340                 345                 350

Asn Leu Trp Leu Asp Gly Lys Gln Asn Thr Val Pro Leu Glu Thr Val
            355                 360                 365

Lys Thr Asn Lys Lys Asn Val Thr Val Gln Glu Leu Asp Leu Gln Ala
            370                 375                 380

Arg Arg Tyr Leu Gln Glu Lys Tyr Asn Leu Tyr Asn Ser Asp Val Phe
385                 390                 395                 400

Asp Gly Lys Val Gln Arg Gly Leu Ile Val Phe His Thr Ser Thr Glu
            405                 410                 415

Pro Ser Val Asn Tyr Asp Leu Phe Gly Ala Gln Gly Gln Tyr Ser Asn
            420                 425                 430

Thr Leu Leu Arg Ile Tyr Arg Asp Asn Lys Thr Ile Asn Ser Glu Asn
```

```
                435                 440                 445
Met His Ile Ala Ile Tyr Leu Tyr Thr Ser Ser Ile Val Met Thr Gln
    450                 455                 460

Thr Pro Thr Ser Leu Leu Val Ser Ala Gly Asp Arg Val Thr Ile Thr
465                 470                 475                 480

Cys Lys Ala Ser Gln Ser Val Ser Asn Asp Val Ala Trp Tyr Gln Gln
                485                 490                 495

Lys Pro Gly Gln Ser Pro Lys Leu Leu Ile Ser Tyr Thr Ser Ser Arg
            500                 505                 510

Tyr Ala Gly Val Pro Asp Arg Phe Ser Gly Ser Gly Ser Gly Thr Asp
        515                 520                 525

Phe Thr Leu Thr Ile Ser Ser Val Gln Ala Glu Asp Leu Ala Val Tyr
    530                 535                 540

Phe Cys Gln Gln Asp Tyr Asn Ser Pro Pro Thr Phe Gly Gly Gly Thr
545                 550                 555                 560

Lys Leu Glu Ile Lys Arg Ala Asp Ala Ala Pro Thr Val Ser Ile Phe
                565                 570                 575

Pro Pro Ser Ser Glu Gln Leu Thr Ser Gly Gly Ala Ser Val Val Cys
            580                 585                 590

Phe Leu Asn Asn Phe Tyr Pro Lys Asp Ile Asn Val Lys Trp Lys Ile
        595                 600                 605

Asp Gly Ser Glu Arg Gln Asn Gly Val Leu Asn Ser Trp Thr Asp Gln
    610                 615                 620

Asp Ser Lys Asp Ser Thr Tyr Ser Met Ser Ser Thr Leu Thr Leu Thr
625                 630                 635                 640

Lys Asp Glu Tyr Glu Arg His Asn Ser Tyr Thr Cys Glu Ala Thr His
                645                 650                 655

Lys Thr Ser Thr Ser Pro Ile Val Lys Ser Phe Asn Arg Asn Glu Ser
            660                 665                 670
```

<210> SEQ ID NO 7
<211> LENGTH: 672
<212> TYPE: PRT
<213> ORGANISM: Artificial Sequence
<220> FEATURE:
<223> OTHER INFORMATION: Mutated and Conjugated Protein
<220> FEATURE:
<221> NAME/KEY: MISC_FEATURE
<222> LOCATION: (459)..(672)
<223> OTHER INFORMATION: Light Chain

<400> SEQUENCE: 7

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110
```

```
Gly Thr Ser Val Thr Val Ser Ser Ala Lys Thr Thr Pro Ser Val
            115                 120                 125
Tyr Pro Leu Ala Pro Gly Ser Ala Ala Gln Thr Asn Ser Met Val Thr
130                 135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                165                 170                 175
Leu Gln Ser Asp Leu Tyr Thr Leu Ser Ser Val Thr Val Pro Ser
            180                 185                 190
Ser Thr Trp Pro Ser Glu Thr Val Thr Cys Asn Val Ala His Pro Ala
        195                 200                 205
Ser Ser Thr Lys Val Asp Lys Lys Ile Val Pro Arg Asp Ser Gly Gly
    210                 215                 220
Pro Ser Glu Lys Ser Glu Glu Ile Asn Glu Lys Asp Leu Arg Lys Lys
225                 230                 235                 240
Ser Glu Leu Gln Gly Thr Ala Leu Gly Asn Leu Lys Gln Ile Tyr Tyr
                245                 250                 255
Tyr Asn Ser Lys Ala Ile Thr Ser Ser Glu Lys Ser Ala Asp Gln Phe
            260                 265                 270
Leu Thr Asn Thr Leu Leu Phe Lys Gly Phe Phe Thr Gly His Pro Trp
        275                 280                 285
Tyr Asn Asp Leu Leu Val Asp Leu Gly Ser Thr Ala Ala Thr Ser Glu
    290                 295                 300
Tyr Glu Gly Ser Ser Val Asp Leu Tyr Gly Ala Tyr Tyr Gly Tyr Gln
305                 310                 315                 320
Cys Ala Gly Gly Thr Pro Asn Lys Thr Ala Cys Met Tyr Gly Gly Val
                325                 330                 335
Thr Leu His Asp Asn Asn Arg Leu Thr Glu Glu Lys Lys Val Pro Ile
            340                 345                 350
Asn Leu Trp Ile Asp Gly Lys Gln Thr Thr Val Pro Ile Asp Lys Val
        355                 360                 365
Lys Thr Ser Lys Lys Glu Val Thr Val Gln Glu Leu Asp Leu Gln Ala
    370                 375                 380
Arg His Tyr Leu His Gly Lys Phe Gly Leu Tyr Asn Ser Asp Ser Phe
385                 390                 395                 400
Gly Gly Lys Val Gln Arg Gly Leu Ile Val Phe His Ser Ser Glu Gly
                405                 410                 415
Ser Thr Val Ser Tyr Asp Leu Phe Asp Ala Gln Gly Gln Tyr Pro Asp
            420                 425                 430
Thr Leu Leu Arg Ile Tyr Arg Asp Asn Thr Thr Ile Ser Ser Thr Ser
        435                 440                 445
Leu Ser Ile Ser Leu Tyr Leu Tyr Thr Thr Ser Ile Val Met Thr Gln
    450                 455                 460
Thr Pro Thr Ser Leu Leu Val Ser Ala Gly Asp Arg Val Thr Ile Thr
465                 470                 475                 480
Cys Lys Ala Ser Gln Ser Val Ser Asn Asp Val Ala Trp Tyr Gln Gln
                485                 490                 495
Lys Pro Gly Gln Ser Pro Lys Leu Leu Ile Ser Tyr Thr Ser Ser Arg
            500                 505                 510
Tyr Ala Gly Val Pro Asp Arg Phe Ser Gly Ser Gly Tyr Gly Thr Asp
        515                 520                 525
Phe Thr Leu Thr Ile Ser Ser Val Gln Ala Glu Asp Ala Ala Val Tyr
```

```
              530                 535                 540
Phe Cys Gln Gln Asp Tyr Asn Ser Pro Pro Thr Phe Gly Gly Gly Thr
545                 550                 555                 560

Lys Leu Glu Ile Lys Arg Ala Asp Ala Ala Pro Thr Val Ser Ile Phe
                565                 570                 575

Pro Pro Ser Ser Glu Gln Leu Thr Ser Gly Gly Ala Ser Val Val Cys
            580                 585                 590

Phe Leu Asn Asn Phe Tyr Pro Lys Asp Ile Asn Val Lys Trp Lys Ile
        595                 600                 605

Asp Gly Ser Glu Arg Gln Asn Gly Val Leu Asn Ser Trp Thr Asp Gln
    610                 615                 620

Asp Ser Lys Asp Ser Thr Tyr Ser Met Ser Ser Thr Leu Thr Leu Thr
625                 630                 635                 640

Lys Asp Glu Tyr Glu Arg His Asn Ser Tyr Thr Cys Glu Ala Thr His
                645                 650                 655

Lys Thr Ser Thr Ser Pro Ile Val Lys Ser Phe Asn Arg Asn Glu Ser
            660                 665                 670

<210> SEQ ID NO 8
<211> LENGTH: 458
<212> TYPE: PRT
<213> ORGANISM: Artificial Sequence
<220> FEATURE:
<223> OTHER INFORMATION: Synthetic polypeptide

<400> SEQUENCE: 8

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser Pro Gly Lys Gly Leu Glu Trp Ile
            35                  40                  45

Gly Arg Ile Asn Pro Asn Asn Gly Val Thr Leu Tyr Asn Gln Lys Phe
        50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Ser Gly Gly
    210                 215                 220

Pro Ser Glu Lys Ser Glu Glu Ile Asn Glu Lys Asp Leu Arg Lys Lys
```

```
            225                 230                 235                 240
Ser Glu Leu Gln Gly Thr Ala Leu Gly Asn Leu Lys Gln Ile Tyr Tyr
                245                 250                 255

Tyr Asn Ser Lys Ala Ile Thr Ser Ser Glu Lys Ser Ala Asp Gln Phe
            260                 265                 270

Leu Thr Asn Thr Leu Leu Phe Lys Gly Phe Phe Thr Gly His Pro Trp
        275                 280                 285

Tyr Asn Asp Leu Leu Val Asp Leu Gly Ser Thr Ala Ala Thr Ser Glu
    290                 295                 300

Tyr Glu Gly Ser Ser Val Asp Leu Tyr Gly Ala Tyr Gly Tyr Gln
305                 310                 315                 320

Cys Ala Gly Gly Thr Pro Asn Lys Thr Ala Cys Met Tyr Gly Val
                325                 330                 335

Thr Leu His Asp Asn Asn Arg Leu Thr Glu Glu Lys Lys Val Pro Ile
                340                 345                 350

Asn Leu Trp Ile Asp Gly Lys Gln Thr Thr Val Pro Ile Asp Lys Val
                355                 360                 365

Lys Thr Ser Lys Lys Glu Val Thr Val Gln Glu Leu Asp Leu Gln Ala
        370                 375                 380

Arg His Tyr Leu His Gly Lys Phe Gly Leu Tyr Asn Ser Asp Ser Phe
385                 390                 395                 400

Gly Gly Lys Val Gln Arg Gly Leu Ile Val Phe His Ser Ser Glu Gly
                405                 410                 415

Ser Thr Val Ser Tyr Asp Leu Phe Asp Ala Gln Gly Gln Tyr Pro Asp
                420                 425                 430

Thr Leu Leu Arg Ile Tyr Arg Asp Asn Thr Thr Ile Ser Ser Thr Ser
            435                 440                 445

Leu Ser Ile Ser Leu Tyr Leu Tyr Thr Thr
        450                 455

<210> SEQ ID NO 9
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 9

Ser Ile Val Met Thr Gln Thr Pro Thr Ser Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Ser Tyr Thr Ser Ser Arg Tyr Ala Gly Val Pro Asp Arg Phe Ser Gly
    50                  55                  60

Ser Gly Tyr Gly Thr Asp Phe Thr Leu Thr Ile Ser Ser Val Gln Ala
65                  70                  75                  80

Glu Asp Ala Ala Val Tyr Phe Cys Gln Gln Asp Tyr Asn Ser Pro Pro
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
```

```
                130                 135                 140
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Ser
    210

<210> SEQ ID NO 10
<211> LENGTH: 233
<212> TYPE: PRT
<213> ORGANISM: Artificial Sequence
<220> FEATURE:
<223> OTHER INFORMATION: Mutated Protein

<400> SEQUENCE: 10

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
                20                  25                  30

Asn Glu Lys Ala Ile Thr Glu Asn Lys Glu Ser Asp Asp Gln Phe Leu
                35                  40                  45

Glu Asn Thr Leu Leu Phe Lys Gly Phe Phe Thr Gly His Pro Trp Tyr
50                  55                  60

Asn Asp Leu Leu Val Asp Leu Gly Ser Lys Asp Ala Thr Asn Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
                100                 105                 110

Leu His Asp Asn Asn Arg Leu Thr Glu Glu Lys Lys Val Pro Ile Asn
                115                 120                 125

Leu Trp Ile Asp Gly Lys Gln Thr Thr Val Pro Ile Asp Lys Val Lys
130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
                180                 185                 190

Thr Val Ser Tyr Asp Leu Phe Asp Ala Gln Gly Gln Tyr Pro Asp Thr
                195                 200                 205

Leu Leu Arg Ile Tyr Arg Asp Asn Lys Thr Ile Asn Ser Glu Asn Leu
                210                 215                 220

His Ile Ala Leu Tyr Leu Tyr Thr Thr
225                 230
```